(12) United States Patent
Wallace et al.

(10) Patent No.: US 9,839,352 B2
(45) Date of Patent: Dec. 12, 2017

(54) SYSTEM, METHOD AND APPARATUS FOR ENABLING CORNEAL TOPOGRAPHY MAPPING BY SMARTPHONE

(71) Applicant: Smart EyeDeas I, LLC, Los Angeles, CA (US)

(72) Inventors: David A Wallace, Los Angeles, CA (US); Edwin J Sarver, Cookeville, TN (US)

(*) Notice: Subject to any disclaimer, the term of this patent is extended or adjusted under 35 U.S.C. 154(b) by 0 days.

(21) Appl. No.: 15/236,366

(22) Filed: Aug. 12, 2016

(65) Prior Publication Data

US 2017/0042421 A1     Feb. 16, 2017

Related U.S. Application Data

(60) Provisional application No. 62/205,669, filed on Aug. 15, 2015.

(51) Int. Cl.
*A61B 3/107* (2006.01)
*A61B 3/00* (2006.01)
(Continued)

(52) U.S. Cl.
CPC ............ *A61B 3/107* (2013.01); *A61B 3/0025* (2013.01); *A61B 3/135* (2013.01); *A61B 3/152* (2013.01);
(Continued)

(58) Field of Classification Search
USPC ................................................ 351/200–246
See application file for complete search history.

(56) References Cited

U.S. PATENT DOCUMENTS

| 4,772,155 A | 9/1988 | Gersten et al. |
| 4,863,260 A | 9/1989 | Gersten et al. |

(Continued)

FOREIGN PATENT DOCUMENTS

| BR | 102013031050 | 3/2015 |
| BR | 102012010884 | 12/2016 |

(Continued)

OTHER PUBLICATIONS

Written Opinion of the International Searching Authority, PCT Application No. PCT/US2016/046948, International Filing Date Aug. 14, 2016 (Aug. 14, 2016); dated Mar. 28, 2017.
(Continued)

*Primary Examiner* — Mohammed Hasan
(74) *Attorney, Agent, or Firm* — Mark R. Kendrick

(57) ABSTRACT

An apparatus for enabling corneal topography includes an attachment to align a placido disc illumination system with a camera of a mobile communication device. The placido disc illumination system generates concentric rings and reflects the concentric rings off a cornea. A portion of the reflected concentric rings are utilized to confirm vertex distance. The apparatus further comprises a memory, a processor, and computer-readable instructions in a mobile communication device. The camera captures an image of reflected concentric rings and communicates the captured image of the reflected concentric rings to an external computing device. A method for performing corneal topography utilizes a mobile computing and/or communication device, projects a plurality of peripheral concentric rings onto a subject's cornea and projects center rings onto the subject's cornea. The method further includes capturing, via a smartphone camera, an image of the projected peripheral concentric rings and the center rings.

13 Claims, 20 Drawing Sheets

(51) Int. Cl.
  *A61B 5/00* (2006.01)
  *A61B 3/15* (2006.01)
  *A61B 3/135* (2006.01)
(52) U.S. Cl.
  CPC ............ *A61B 3/154* (2013.01); *A61B 5/0022* (2013.01); *A61B 5/6898* (2013.01)

(56) References Cited

U.S. PATENT DOCUMENTS

| | | | |
|---|---|---|---|
| 5,009,498 | A | 4/1991 | Gersten et al. |
| 5,018,850 | A | 5/1991 | Gersten et al. |
| 5,416,539 | A | 5/1995 | Gersten et al. |
| 6,152,565 | A | 11/2000 | Liu et al. |
| 7,255,440 | B2 | 8/2007 | Hanebuchi |
| 7,370,969 | B2 | 5/2008 | Klyce et al. |
| 7,611,245 | B2 | 11/2009 | Carbonari |
| 8,926,095 | B2 | 1/2015 | Bartels |
| 9,351,637 | B2 | 5/2016 | Shimizu |
| 9,427,156 | B1* | 8/2016 | Steven ................. A61B 3/18 |
| 9,545,200 | B2 | 1/2017 | Catanzariti et al. |
| 2008/0204659 | A1* | 8/2008 | Carbonari ............. A61B 3/107 351/212 |
| 2011/0273669 | A1* | 11/2011 | Abitbol ................ A61B 3/1015 351/212 |
| 2012/0320340 | A1 | 12/2012 | Coleman, III |
| 2015/0313462 | A1 | 11/2015 | Reis |
| 2016/0000322 | A1* | 1/2016 | Farrer ................... A61B 3/107 351/212 |
| 2016/0198946 | A1 | 7/2016 | Zhou |

FOREIGN PATENT DOCUMENTS

| | | |
|---|---|---|
| CN | 201986004 | 9/2011 |
| CN | 102946790 | 2/2013 |
| CN | 204618187 | 9/2015 |
| CN | 205163030 | 4/2016 |
| DE | 10201500964 | 1/2017 |
| EP | 0 589 857 A1 | 3/1994 |
| EP | 1488733 A2 | 12/2004 |
| JP | 2007 000382 | 1/2007 |
| WO | WO 99/33393 A1 | 7/1999 |
| WO | WO 2004/017825 A1 | 3/2004 |

OTHER PUBLICATIONS

Notification of Transmittal of International Search Report and the Written Opinion of the International Searching Authority, PCT Application No. PCT/US2016/046948, dated Mar. 28, 2017.
Pinheiro et al., "Design and Development of an Ultraportable Corneal Topographer for Smartphones as a Low Cost New Tool for Preventing Blindness Caused by Keratoconus."
International Journal of Latest Research in Science and Technology; ISSN (Online):2278-5299; vol. 4, Issue 3: p. 72-76, May-Jun. 2015.
Andre Luis Beling Da Rosa, "An Acessible Approach to Corneal Topography," Master's Thesis, Computer Science, Porto Alegre, Dec. 2013.

* cited by examiner

SYSTEM, METHOD AND APPARATUS FOR ENABLING CORNEAL TOPOGRAPHY MAPPING BY SMARTPHONE

RELATED APPLICATIONS

This application claims priority to provisional application Ser. No. 62/205,669, filed Aug. 15, 2015, entitled "System and Method Enabling Corneal Topography Mapping by Smartphone," the disclosure of which is hereby incorporated by reference.

BACKGROUND

1. Field

The subject matter disclosed herein relates to an apparatus, system and method of enabling corneal topography by mobile communication and/or computing devices, and more specifically a smartphone.

2. Information/Background of the Invention

Corneal topography has evolved to become a key diagnostic modality in numerous sectors of eye care including routine eye examination, evaluation for laser refractive surgery (LASIK and PRK), evaluation for cataract and lens implant surgery, and evaluation or monitoring of numerous corneal disease states including keratoconus. Commercial corneal topography devices currently in use typically incorporate an illuminated series of concentric rings (a "placido disc") viewed coaxially by a cornea being tested. A digitized image is obtained of the reflected rings.

Most commercially available corneal topography systems evolved as standalone diagnostic instruments connected to a dedicated personal computer. The placido disc is mounted in front of an apparatus for stabilization of the subject's head, typically situated on a special motorized table intended to be positioned comfortably in front of a seated patient. The rings image is processed by proprietary software resident on the computer to which a placido disc system is affixed, and is typically stored locally on the dedicated computer or a network server in association with patient identifying information for later retrieval, comparison, and additional analysis. Power maps and other derivative analyses are typically displayed on a computer monitor, and are output to a printer or communicated electronic medical record ("EMR") databases in various formats. The relative high cost ($8,000 to over $50,000) and specialized nature of these devices causes their use to be largely limited to the offices of corneal specialists, laser vision correction surgeons, cataract surgeons, and offices of eye care professionals (ophthalmologists or optometrists) performing a large number of routine eye examinations.

Relative high cost and lack of portability inherently limit the reach of corneal topography to other healthcare professionals who may desire to use this diagnostic modality for screening purposes or other applications. For instance, keratoconus is a condition characterized by abnormalities of corneal topography including asymmetry of topographic power, abnormal maximum central steepness, reduced corneal thickness in the apex of the "cone" or zone of maximum steepness, and decentered corneal apex, among other abnormalities. The incidence of keratoconus in the general population is estimated to be in the range of 1 in several hundred. Keratoconus typically becomes manifest in the age range 18-26 years, and occasionally in younger patients. Therefore, there is reason for pediatricians and school nurses, among other groups, to have access to a cost-effective, portable method to screen for this condition.

U.S. Pat. No. 5,526,073 discloses a small cone corneal topographer with concentric black and white rings. The corneal vertex location in this method was based on the vertex breaking a beam of light. This method described in this patent suffers from a trade-off of allowing a wide object field of view and small rings in the center of the cornea.

U.S. Pat. No. 7,465,049 discloses several ophthalmic systems utilizing a cellular phone. The method and corneal topography system described in U.S. Pat. No. 7,465,049 does not include a ring target generation technique where both a wide object field of view and small reflected rings are provided.

U.S. Pat. No. 9,036,282 discloses a method for attaching a lens to a system such as a smartphone. This method disclosed in U.S. Pat. No. 9,036,282 is very general and does not describe how it could be used with a portable corneal topography system.

U.S. Pat. No. 9,066,683 discloses a method of using a smartphone with a custom hardware module for measuring the wavefront of an eye. The method disclosed in U.S. Pat. No. 9,066,683 does not describe how it could be applied to a portable corneal topography system.

U.S. Pat. No. 9,163,936 discloses a three-dimensional surface profilometer for use in metrology and other applications. The methods disclosed in U.S. Pat. No. 9,163,936 describes the use of a smartphone, but do not describe how they could be applied to realize a reflected ring corneal topography system.

A system is described in a thesis entitled "An Accessible Approach to Corneal Topography"; Andre Luis Beling da Rosa. This system uses a concentric ring target and is integrated with a smartphone, but it does not simultaneously observe a wide object field of view, measure small central corneal zones, and provide for location of the corneal vertex during image acquisition.

"Design and Development of an Ultraportable Corneal Topographer for a Smartphone as a Low Cost New Tool for Preventing Blindness Caused by Keratoconous" by Pinheiro et al. ("Pinheiro") discloses a corneal topography system that employs a 3D printed ring target and shell to allow attachment to a smartphone. This system does not simultaneously observe a wide object field of view, measure small central corneal zones, and provide for location of the corneal vertex during image acquisition. The limitations of the systems described above are overcome by our invention, the description which is provided below.

BRIEF DESCRIPTION OF DRAWINGS

Non-limiting and non-exhaustive aspects are described with reference to the following figures, wherein like reference numerals refer to like parts throughout the various figures unless otherwise specified.

DETAILED DESCRIPTION

Figure 1:
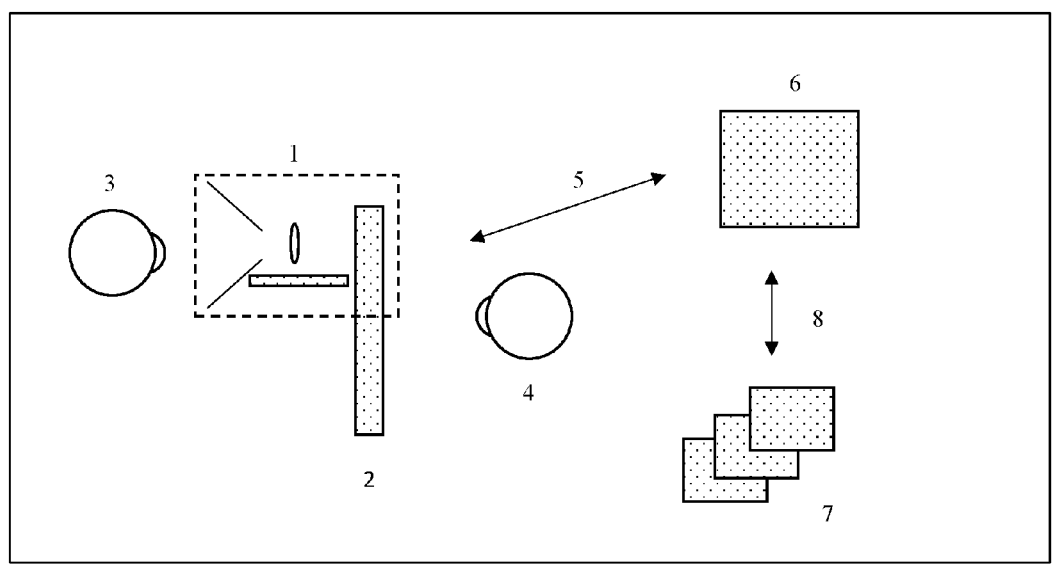
FIG. 1 illustrates a corneal topography system according to embodiments.

In the following detailed description, numerous specific details are set forth to provide a thorough understanding of claimed subject matter. For purposes of explanation, specific numbers, systems and/or configurations are set forth, for example. However, it should be apparent to one skilled in the relevant art having benefit of this disclosure that claimed subject matter may be practiced without specific details. In other instances, well-known features may be omitted and/or simplified so as not to obscure claimed subject matter. While certain features have been illustrated and/or described herein, many modifications, substitutions, changes and/or equivalents may occur to those skilled in the art. It is, therefore, to be understood that appended claims are intended to cover any and all modifications and/or changes as fall within claimed subject matter.

References throughout this specification to one implementation, an implementation, one embodiment, embodiments, an embodiment and/or the like means that a particular feature, structure, and/or characteristic described in connection with a particular implementation and/or embodiment is included in at least one implementation and/or embodiment of claimed subject matter. Thus, appearances of such phrases, for example, in various places throughout this specification are not necessarily intended to refer to the same implementation or to any one particular implementation described. Furthermore, it is to be understood that particular features, structures, and/or characteristics described are capable of being combined in various ways in one or more implementations and, therefore, are within intended claim scope, for example. In general, of course, these and other issues vary with context. Therefore, particular context of description and/or usage provides helpful guidance regarding inferences to be drawn.

In this context, the terms "coupled", "connected," and/or similar terms are used generically. It should be understood that these terms are not intended as synonyms. Rather, "connected" is used generically to indicate that two or more components, for example, are in direct physical, including electrical, contact; while, "coupled" is used generically to mean that two or more components are potentially in direct physical, including electrical, contact; however, "coupled" is also used generically to also mean that two or more components are not necessarily in direct contact, but nonetheless are able to co-operate and/or interact. The term coupled is also understood generically to mean indirectly connected, for example, in an appropriate context. In a context of this application, if signals, instructions, and/or commands are transmitted from one component (e.g., a controller or processor) to another component (or apparatus), it is understood that signals, instructions, and/or commands may be transmitted directly to a component, or may pass through a number of other components on a way to a destination component.

The terms, "and", "or", "and/or" and/or similar terms, as used herein, include a variety of meanings that also are expected to depend at least in part upon the particular context in which such terms are used. Typically, "or" if used to associate a list, such as A, B or C, is intended to mean A, B, and C, here used in the inclusive sense, as well as A, B or C, here used in the exclusive sense. In addition, the term "one or more" and/or similar terms is used to describe any feature, structure, and/or characteristic in the singular and/or is also used to describe a plurality and/or some other combination of features, structures and/or characteristics. Likewise, the term "based on" and/or similar terms are understood as not necessarily intending to convey an exclusive set of factors, but to allow for existence of additional factors not necessarily expressly described. Of course, for all of the foregoing, particular context of description and/or usage provides helpful guidance regarding inferences to be drawn. It should be noted that the following description merely provides one or more illustrative examples and claimed subject matter is not limited to these one or more illustrative examples; however, again, particular context of description and/or usage provides helpful guidance regarding inferences to be drawn.

Mobile communication and/or computing devices (e.g., smartphones) now include a high-resolution camera and a processor having sufficient processing power to perform numerous dedicated tasks. Although the description herein may refer to a smartphone, the description provided herein applies to other mobile communication and/or computing devices (e.g., tablets, laptops, PDAs, wearable technology). In embodiments, numerous tasks may be performed using computer-readable and executable instructions stored in a memory of a smartphone and/or also utilizing internal and/or external sensors attached and/or coupled to a smartphone. It is estimated that by the year 2020, roughly 80% of adults in the world may utilize and/or operate a smartphone. In embodiments, cellular and Wi-Fi networks, to which smartphones are connected and/or coupled, make it possible to communicate, transmit, receive, store, process and evaluate data, measurements, and/or images communicated, transmitted and/or received from external computing devices (e.g., centralized, application, mobile application and/or loud-based servers).

In embodiments, described herein is a system and method for performing corneal topography using a placido disc system that may be attached, connected and/or coupled to a mobile communication and/or computing device (e.g., a smartphone). In embodiments, a software application ("app") resident on a mobile communication and/or computing device (e.g., computer-readable instructions stored on a memory of a mobile communication and/or computing device) may receive subject characteristics and/or measurements, facilitate and/or capture images of rings projected and/or reflected from a placido disk; analyze measurements, data or images; communicate captured images, related user characteristics and/or measurements, and/or captured image related parameters and/or measurements to an external computing device via a network (e.g., a central server, an application server, a mobile application server, and/or cloud-based servers); receive communicated power maps and/or related measurements and/or data; and display power maps on a display screen. In embodiments, a mobile communication and/or computing device (e.g., smartphone) may be utilized as a platform for hosting, connecting to, attaching to and/or coupling to corneal topography hardware (e.g., portable and/or stationary hardware and apparatuses) due to its widespread use and suitability and also because it comprises several components, devices, and/or circuits utilized by a corneal topography system.

In embodiments, for example, a mobile communication and/or computing device (e.g., smartphone) may comprise a display, a processor, a memory, a camera, an illumination system (e.g., one or more lights such as LED lights), a wireless transceiver, and/or a network transceiver. In embodiments, a wireless transceiver and associated circuitry and/or software may communicate utilizing cellular networks and/or localized wireless networks using 802.11g standards, which may be referred to as "Wi-Fi" networks. In utilizing components, devices and/or circuits commonly resident in mobile communication and/or computing device (e.g., smartphones), an overall cost of a corneal topography system may be dramatically reduced, and such a corneal topography system may be much more portable and/or able to be utilized with a variety of existing hardware than prior systems. In embodiments, communication of images and related characteristics and/or measurements to a remote computing device and/or server (e.g., a web-based (rather than LAN-based) server) may provide additional opportunities for remote and/or long-term storage of captured images and related characteristics and/or measurements, additional and more-nuanced analysis of captured images and related characteristics and/or measurements, comparison analysis or "difference mapping" identifying changes over time, and certain additional levels of analysis commonly considered "big data" types of applications.

FIG. 1 illustrates a corneal topography system according to embodiments. In embodiments, as illustrated in FIG. 1, a corneal topography apparatus 1 may be attached to a mobile communication and/or computing device (e.g., smartphone) 2. In embodiments, a corneal topography apparatus 1 may be snapped onto a smartphone 2. In embodiments, a corneal topography apparatus 1 may be coupled to, connected to, adhered to, and/or attached to a smartphone 2. In embodiments, a smartphone 2 may include a memory, a processor, and computer-readable instructions which are loaded into a memory and executed by a processor to execute a topography application (e.g., topography software application or "app"). In embodiments, a corneal examination may be performed and an image of the patient's eye 3 may be viewed by an operator 4 on a display device (e.g., a smartphone display and/or a separate display device). In embodiments, an image of rings may be reflected off a patient's cornea and captured by a camera of a smartphone 2. In embodiments, images of rings may be captured by a camera of a smartphone 2. In embodiments, an image of rings may be transmitted 5 via a communications network (e.g., an internet and/or a wireless communication network) to a repository computing device 6 (e.g., a central computing device, an application server, a mobile application server, and/or a cloud-based server). In embodiments, a repository computing device 6 may process and/or analyze a communicated image. In embodiments, a repository computer 6 may perform analysis on the communicated image (e.g., such as to determine which graphics display to generate). In embodiments, a repository computer 6 may communicate analysis results (e.g., a corneal topography map and/or related measurements) to a smartphone 2. In embodiments, analysis results may be displayed on a smartphone display. In embodiments, analysis results may be communicated to a secondary computing device 7 via communications links such as transmission channel 8 (e.g., wireless communication networks, communication networks). In embodiments, the communicated image, measurements and/or analysis data related to and referencing the communicated image may be stored on a repository computing device 6. In embodiments, the communicated image, measurements and/or analysis data may be utilized to evaluate and/or analyze changes in the corneal shape due to surgery, disease, or the aging process. In embodiments, computing devices external to a repository computing device 6 (e.g., authorized remote stations) may access results of all stored data (e.g., communicated images, measurements and/or analysis results and/or data) and may further process the stored data to comparison mapping software maintenance and enhancement, research, billing reports, and other uses.

In embodiments, an apparatus for enabling corneal topography comprises an attachment to align a placido disc illumination system with a camera of a mobile communication device. The placido disc illumination system generates concentric rings, and reflects the concentric rings off a cornea, a portion of the reflected concentric rings being utilized to confirm vertex distance. The apparatus further comprises a memory, a processor, and computer-readable instructions in a mobile communication device, the camera capturing an image of the reflected concentric ring and communicating the captured image and/or images of reflected concentric rings to an external computing device. In embodiments, the computer-readable instructions may be loaded into the memory and executable by a processor to receive an indication of a correct vertex distance and capture an image or images of the reflected concentric rings if the indication is received. In embodiments, a specific concentric image may be displayed when a cornea is at a desired vertex distance and different concentric ring images identify a cornea being closer than or further away from the desired vertex distance. In embodiments, the software (executed computer-readable instructions) may calculate image quality of the captured image or images. In embodiments, the software (executed computer-readable instructions) may communicate a captured image and related measurements to an external computing device if the image quality is greater than a defined threshold. In embodiments, an external computing device may analyze the captured image and generate a corneal topography map of the subject's cornea and/or generate additional clinical interpretations. In embodiments, the external computing device calculate and/or compute a vertex distance. In embodiments, the external computing device may be one or more of a remote computing device, a medical records repository computing device, an email server for a registered user and/or consulting specialist, a medical billing computing device, a second computing device comprising computer-readable instructions executable by a processor to perform additional analysis (e.g., intra-ocular lens ("IOL") power calculation), or a desktop computing device. In embodiments, the apparatus or mobile communication device may receive a generated corneal topography map from the external computing device. In embodiments, the mobile communication device may include a gyroscope, the gyroscope generating rotational information and/or vertical information. In embodiments, the software (executed computer-readable instructions) receives the rotational information and/or vertical information of the mobile communication device and assess the attachment's and/or smartphone' position with respect to a true vertical position. In embodiments, the apparatus may comprise a lighting source, the lighting source to illuminate a placido disc system to assist in generating the projected concentric rings image. In embodiments, the apparatus may comprise a mounting assembly. The mounting assembly mounts the attachment and/or mobile communication device on a slit-lamp microscope to enable comfortable positioning of the apparatus in front of a seated subject.

In embodiments, a placido rings illumination apparatus comprises a truncated cone, an interior of a truncated cone having applied thereon alternating peripheral concentric rings and a plate mounted on a first end of the truncated cone and a plate. In embodiments, the plate has an opening corresponding to an opening at the first end of the truncated cone and having lighting elements. In embodiments, the lighting elements may illuminate the truncated cone to project peripheral concentric rings on a cornea of a subject, where the subject's cornea may be placed in front of the truncated cone. In embodiments, the apparatus may include a central ring projection guide and an additional light source, where the additional light source and central ring projection guide project one or more central concentric rings onto the cornea of the subject. In embodiments, the peripheral concentric rings and the central concentric rings may be utilized as a vertex distance positioning cue. In embodiments, the lighting elements may direct light away from the truncated cone and towards a smartphone camera so that direct observation of the lighting elements by the subject's eye is not possible.

In embodiments, a method or process for performing corneal topography utilizing a mobile computing and/or communication device, comprises projecting a plurality of peripheral concentric rings onto a subject's cornea; and projecting center rings onto the subject's cornea. In embodiments, the method or process further includes capturing, via a smartphone camera, an image or images of the projected peripheral concentric rings and the center ring. In embodiments, the method or process further includes communicating the captured image or images to an external computing device. In embodiments, the method further includes receiving a computed corneal topography map from the external computing device.

Figure 2:
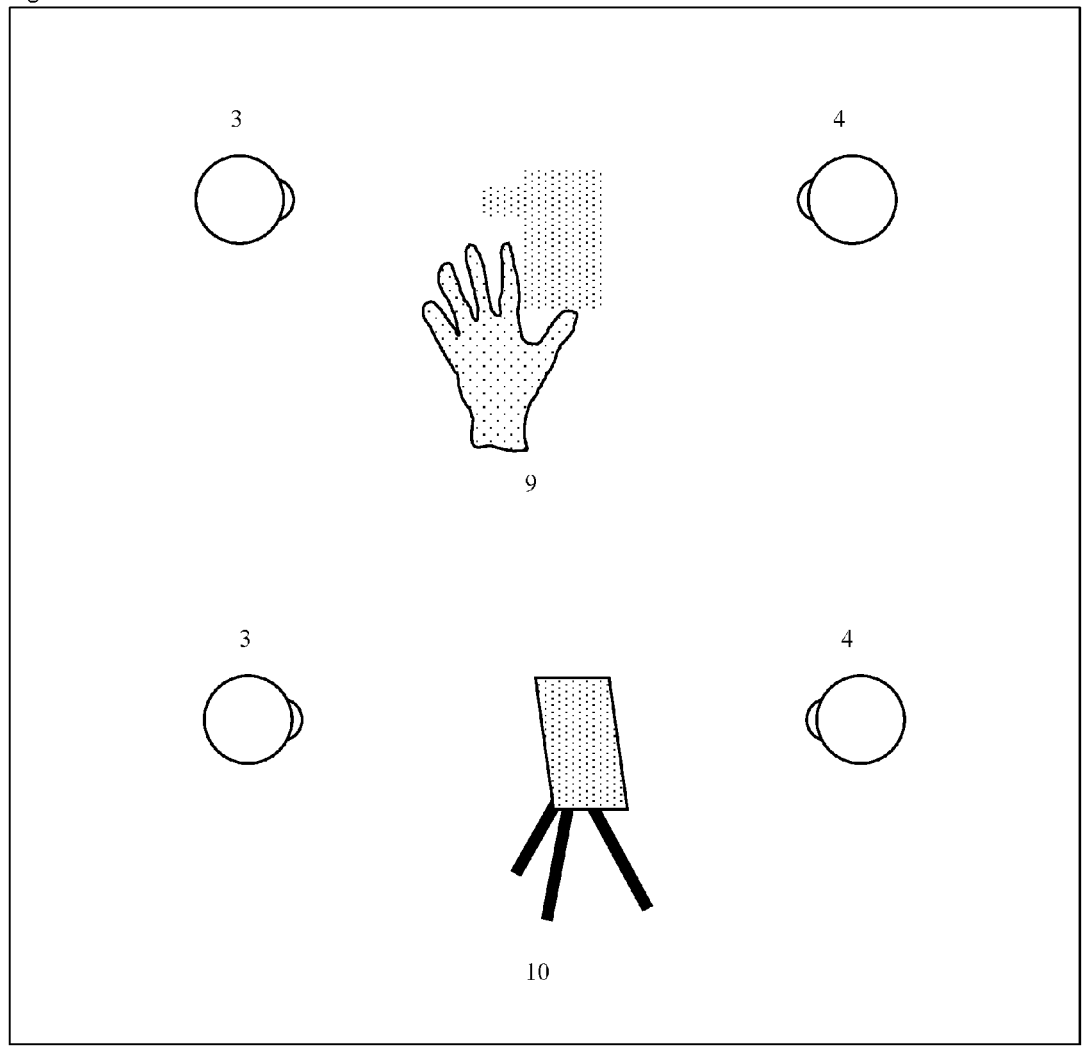
FIG. 2 illustrates a plurality of methods to manipulate a corneal topography system during an acquisition of an image of a cornea during exam according to embodiments.

FIG. 2 illustrates a plurality of methods to manipulate a corneal topography system during an acquisition of an image of a cornea during exam according to embodiments. In embodiments, a first method is for an operator 4 to hold the corneal topography system in a hand 9 while an exam is performed of a subject's eye 3. In embodiments, a second method is to use a simple tripod 10 to stabilize a corneal topography system. In embodiments, a third method is to mount a mobile communication and/or computing device (e.g., the smartphone) to a pivot-point of a slit-lamp microscope arm, allowing positioning through use of a slit-lamp joystick. In embodiments, a fourth method is to provide a customized base for a mobile communication and/or computing device (e.g., the smartphone), chin-rest for a subject, and manipulator to move a customized base and/or chin-rest.

Figure 3:
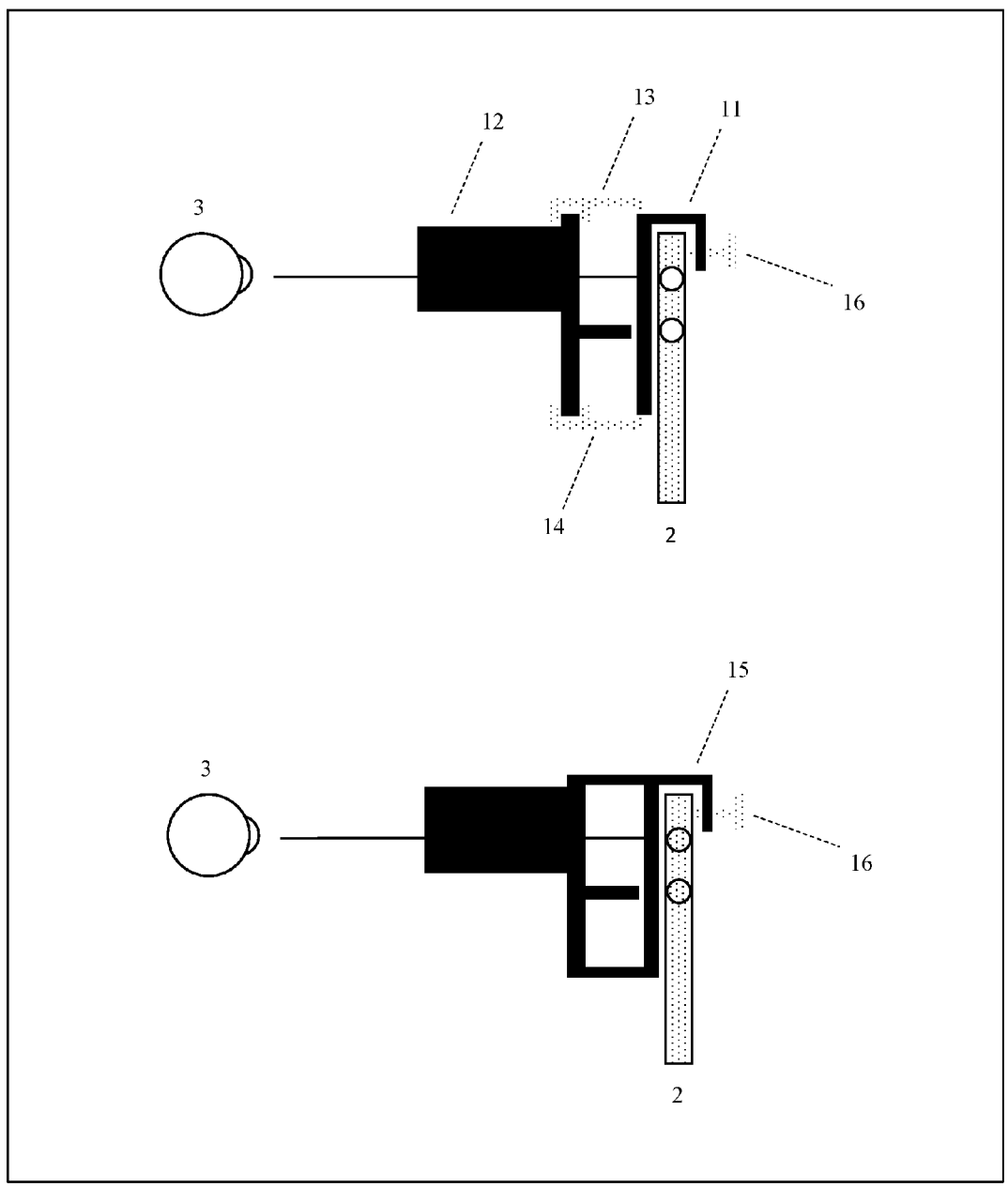
FIG. 3 illustrates two methods and/or devices for attaching corneal topography hardware to a mobile communication and/or computing device.

FIG. 3 illustrates two methods and/or devices for attaching corneal topography hardware to a mobile communication and/or computing device (e.g., the smartphone). In a top part of FIG. 3, a two-part attachment frame is illustrated. In embodiments, one frame part 11 may be attached to a mobile communication and/or computing device 2 (e.g., the smartphone) and may be intended to remain in contact or as part with a mobile communication and/or computing device 2 (e.g., the smartphone), similar to and/or like a protective case or exoskeleton. In embodiments, a second frame part 12 may then be attached, connected, adhered and/or coupled to a first frame part 11 via one or more arms (e.g., two arms 13 and 14), and/or some other snap in, fastener, adhesive, connector, and/or screw. In embodiments, whether elements of a corneal topography hardware or system reside in either of the two frame parts 11 or 12 may likely be decided by market forces and is not a significant factor to overall performance of a corneal topography system. In embodiments, in a lower part of FIG. 3, a simple one frame attachment 15 may attach, couple, adhere and/or connect to a mobile communication and/or computing device 2 (e.g., the smartphone). In this embodiment, corneal topography hardware elements may be integrated into a frame attachment 15 and may be attached as needed to a mobile communication and/or computing device 2 (e.g., the smartphone). In embodiments, a mobile communication and/or computing device 2 (e.g., the smartphone) may be attached to a one-part frame 15 and/or a first frame part 11 and a second frame part 12 utilizing a soft thumb screw 16 (or other fasteners, connectors, snap-in, and/or adhesive).

Figure 4:
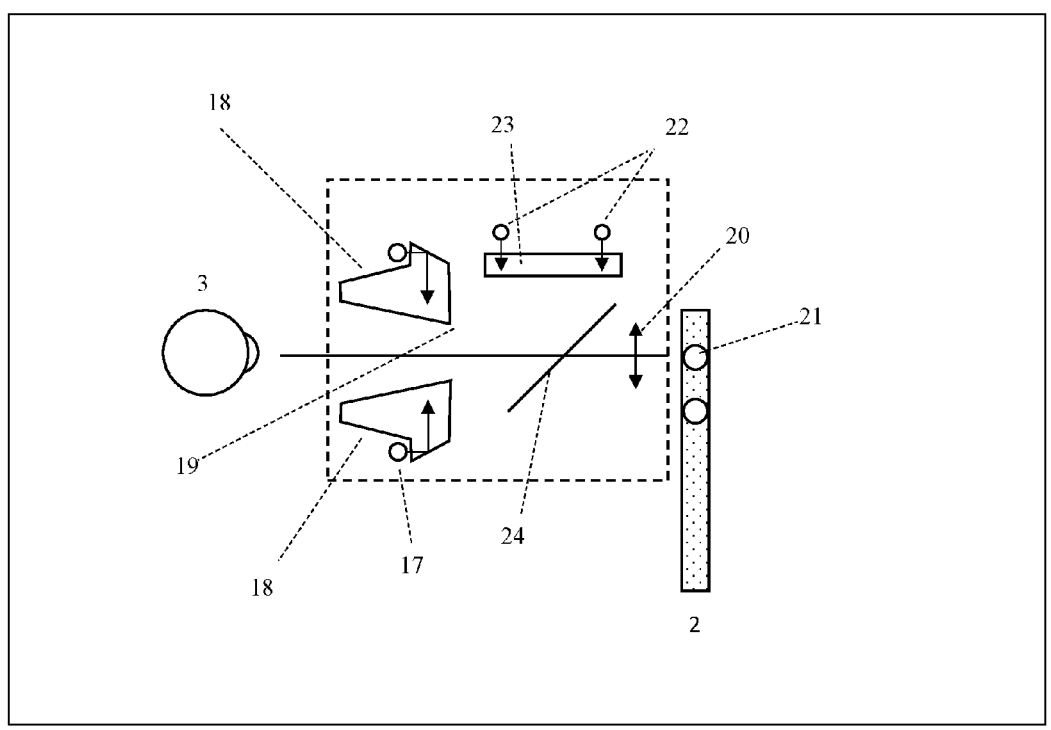
FIG. 4 illustrates a top level layout of a corneal topography apparatus according to embodiments.

A combination of the attachment and/or mobile communication and computing device may be referred to as a corneal topography apparatus. FIG. 4 illustrates a top level layout of a corneal topography apparatus according to embodiments. In embodiments, such as illustrated in FIG. 4, a light source 17 may illuminate a peripheral light guide 18 that is in the shape of cone when viewed from a front view. In embodiments, a light guide 18 may be illustrated in profile in FIG. 4, but a light guide 18 may be symmetrical about a main optical axis. In embodiments, an inside portion of a light guide 18 has concentric rings that block light from light source 17 so that concentric rings are generated that are reflected off a periphery of a cornea. In embodiments, a light guide 18 may have concentric rings on an interior surface. In embodiments, a central aperture 19 of a light guide may be large in order to admit light from a periphery of a cornea into the auxiliary image lens 20 so that a full horizontal meridian of a cornea may be observed by a mobile communication and/or computing device 2 (e.g., smartphone) camera aperture 21. In embodiments, a second illumination source 22 may illuminate a central light guide 23 that is in the shape of a two-dimensional plane when viewed from and/or by a subject's eye 3. In embodiments, a portion of a central light guide 23 that is closest to an optical axis (which may be orthogonal to a plane of FIG. 4) may contain a concentric set of rings that alternatively block and transmit light source 22 to form concentric rings reflecting off a central cornea. In embodiments, both central and peripheral rings are combined via beam splitter 24 to form a continuous set of rings to be reflected off the cornea. A light guide 18 may also be constructed and/or shaped as a cylinder (as with the rings placed on the inside (e.g., inside surface) of a cylinder. In addition to the cone or cylinder shapes, a plane at the end of the cone or cylinder may be added to simplify the addition of the central rings. Other shapes such as portions of ellipsoids, spheres, polynomial, or free form surfaces can be used as the light guide 18 with rings placed on an interior (e.g., an interior surface) of these shapes.

There are four primary purposes for utilizing a combination of central and peripheral light ring sources which are reflected off of a subject's cornea. In embodiments, a first purpose is to allow a wide, unobstructed view of the horizontal meridian of a subject's cornea. In embodiments, a first purpose may be accomplished by the wide aperture 19 at the back of a peripheral rings light guide 18, as illustrated in FIG. 4. In embodiments, a second purpose may be to provide very small rings to be reflected off the cornea for measurements near a center of a subject's cornea. This is an important feature in order to be competitive with other current clinical corneal topography systems. In embodiments, a third purpose is to provide a means of fixation for a subject's eye to align a subject's eye with a corneal topography system optics. In embodiments, a fourth purpose may be to provide a means to accurately position a cornea's vertex distance from a point in an instruments coordinate system. In embodiments, this positioning of the cornea distance may be important for image quality and for accurate corneal measurements.

Figure 5:
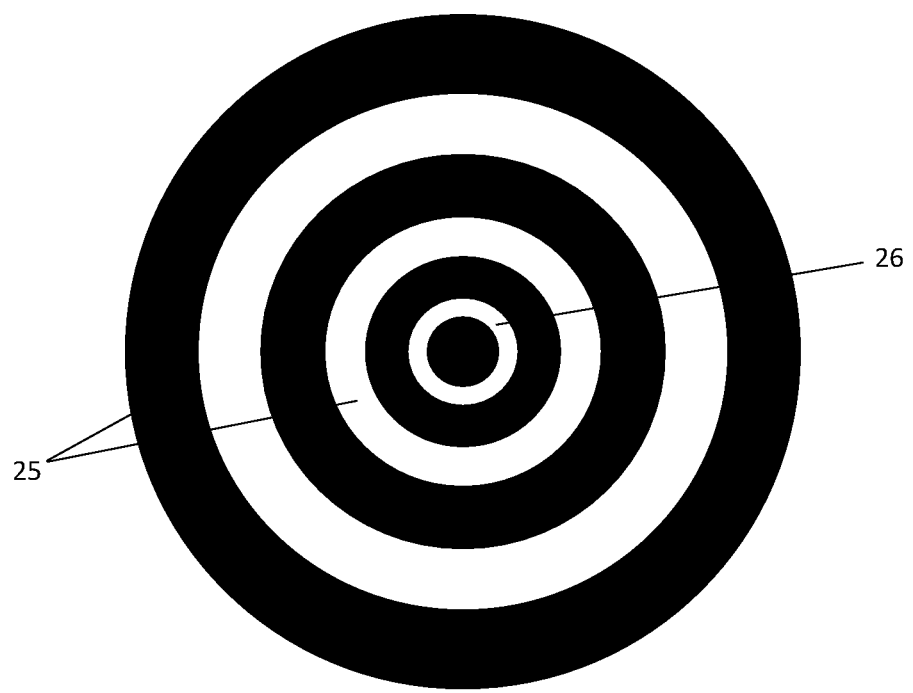
FIG. 5 illustrates a combined reflected rings pattern according to embodiments.

FIG. 5 illustrates a combined reflected rings pattern according to embodiments. In embodiments, as illustrated in FIGS. 4 and 5, peripheral reflected rings 25 and central reflected rings 26 may be reflected off of a subject's cornea and captured by a mobile communication and/or computing device 2 (e.g., smartphone's) camera. In embodiments, a number and/or size of concentric rings may be selected based on the manufacturing capabilities used to manufacture the peripheral rings, and/or other commercial and/or marketing forces. In embodiments, for example, 32 consecutive ring edges (16 white rings) may be employed and/or utilized. In embodiments, a central ring may correspond to a 0.3 mm diameter on an 8 mm sphere and an outside ring may correspond to a 9.5 mm diameter on an 8 mm sphere. In embodiments, locations of other rings of the concentric rings may be calculated to yield evenly spaced reflected rings on an 8 mm sphere. In embodiments, such as illustrated in FIG. 5, a number and size of the concentric rings may not be drawn and/or illustrated to scale.

Figure 8:
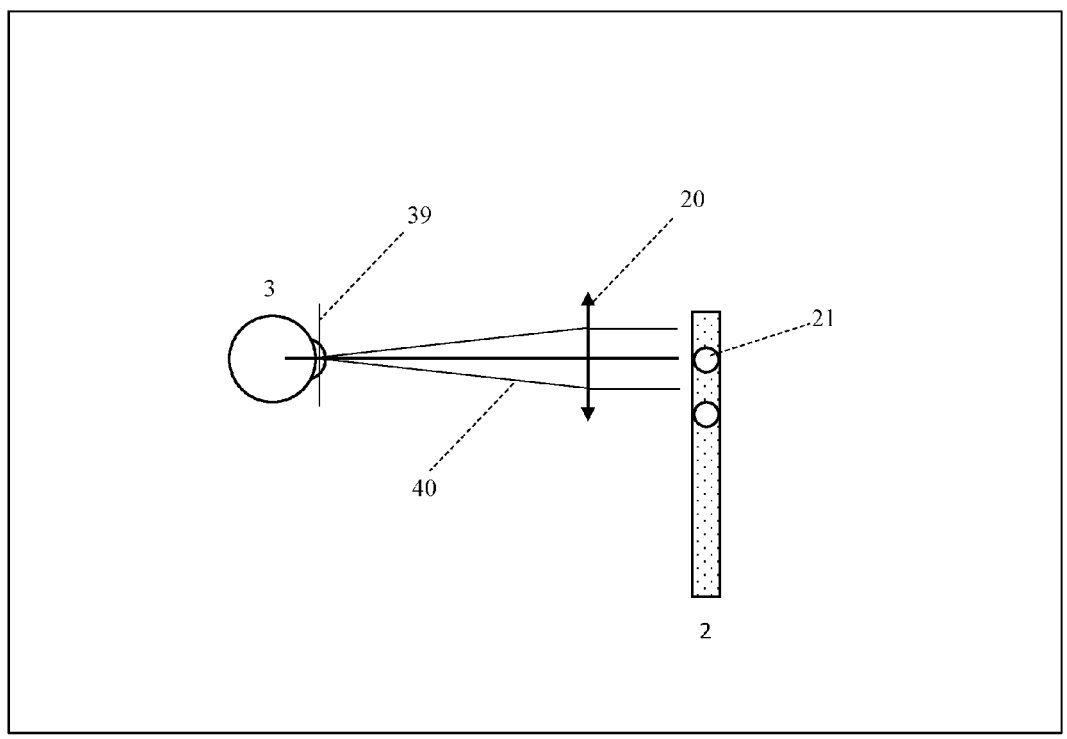
FIG. 8 illustrates the auxiliary image lens in relation to an object plane according to embodiments.

In embodiments, since a center of the concentric rings may be very small, a center of the concentric rings may be used as a fixation location. FIG. 8 illustrates a center of a central white ring. In embodiments, using a center of concentric rings as a fixation point and/or location simplifies a design of a corneal topography system and hence reduces a system's cost. In embodiments, a disadvantage to using a central ring as a fixation location and/or point is that the central ring may be a same color as the concentric rings and accordingly may be difficult for the subject's eye to align with it. In embodiments, an improvement on utilizing a white ring as a fixation point and/or location is to make a central ring a distinguishable color (e.g., make a central ring a green color using, for example, a green LED). In embodiments, a second disadvantage is that a concentric ring may be optically close to a subject's eye and so may not be in focus for a subject's eye. In embodiments, a second improvement to an apparatus may be to place and/or position a lens in front of a central distinguishable spot (e.g., a green spot) and to place the green LED spot at an optical infinity.

In embodiments where a separate LED is used for fixation, in some cases it may be advantageous for the fixation light to be controlled separately from a ring illumination. This provides the ability to use only a fixation light during patient alignment, momentarily flash the concentric rings, and capture a rings image, which may later by analyzed and/or processed. In embodiments utilizing this technique, a patient that is light sensitive may be exposed to a minimum amount of light and discomfort during an examination. In another and/or additional embodiment, a communication channel, such as a Bluetooth, Zigbee, or other wireless or wired local area network communications channel, may be used between a software application on a mobile communication and/or computing device 2 (e.g., the smartphone) and a corneal topography hardware attachment 1 to facilitate the proper synchronization of light sources and exam acquisition.

Figure 6:
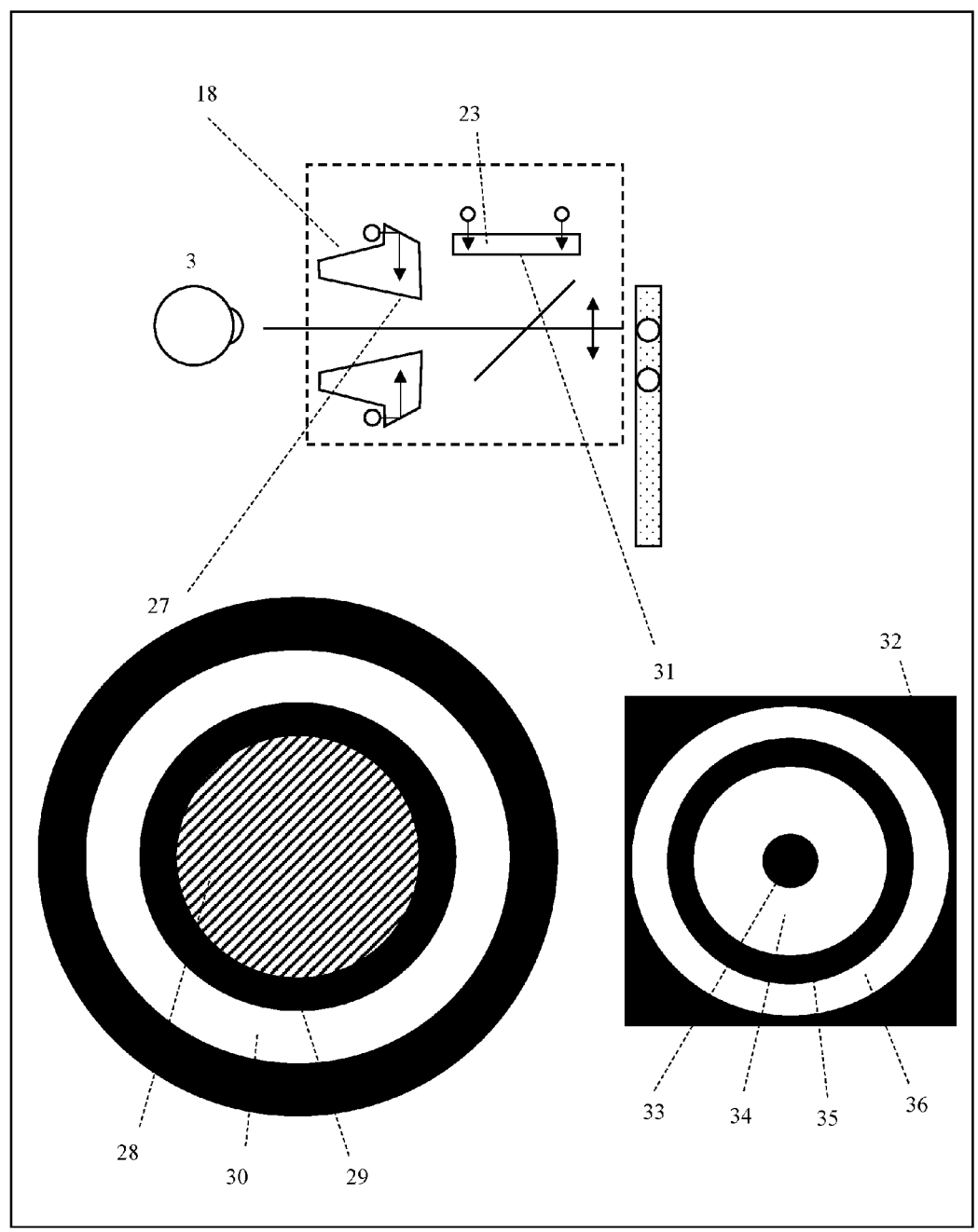
FIG. 6 illustrates details of ring patterns on a peripheral rings light guide and a center rings light guide according to embodiments.

FIG. 6 illustrates details of ring patterns on a peripheral rings light guide 18 and a center rings light guide 23 according to embodiments. In embodiments, peripheral rings pattern 27 shows four concentric regions. In embodiments, as illustrated in FIGS. 4 and 6, a central region 28 of a peripheral rings pattern is shown as hatched lines. In embodiments, the hatched lines represent an area or region of a central aperture of a peripheral rings light guide 18, shown in a bottom left portion FIG. 6. In embodiments, for example, an area or region may be a hole that permits light from a central rings light guide 23, shown in FIG. 6, to reflect off a cornea of a subject and that also permits light reflected off a subject's eye to enter a camera on a mobile communication and/or computing device 2 (e. g., smartphone). In embodiments, as illustrated in FIGS. 4 and 6, a next region 29 may result in and/or project half a black ring for an overall target that reaches a cornea of a subject. In embodiments, a next region 30 may be a full white ring for a target that reaches a cornea of a subject. In embodiments, additional concentric rings (which make up a remainder of the peripheral concentric rings) may be located outside region 30. In embodiments, a left bottom side of FIG. 6 illustrates only one additional concentric ring to rings 28 29 and 30.

In embodiments, such as an embodiment illustrated in a bottom right of FIG. 6, a central rings pattern 31 may show and/or illustrate four concentric ring regions and a bounding square black background 32. In embodiments, a central rings pattern 31 may be placed on and/or in front of a central rings light guide 23, shown in FIGS. 4 and 6. In embodiments, a central region 33 of a central rings pattern 31 may be a black circle and this may set and/or establish a smallest ring diameter of an image reflected off of a subject's cornea. In embodiments, a next region 34 may be a full white ring for a target projection that reaches and/or is projected onto a subject's cornea. In embodiments, a next region 35 may be half a black ring (in terms of width) for a target projection that reaches and/or is projected onto a subject's cornea. In embodiments, an outside white ring 36 of a central rings pattern 31 may only be visible in a reflected rings image off of a subject's cornea when a subject's eye is too close to a mobile communication and/or computing device (e.g., smartphone).

Figure 7:
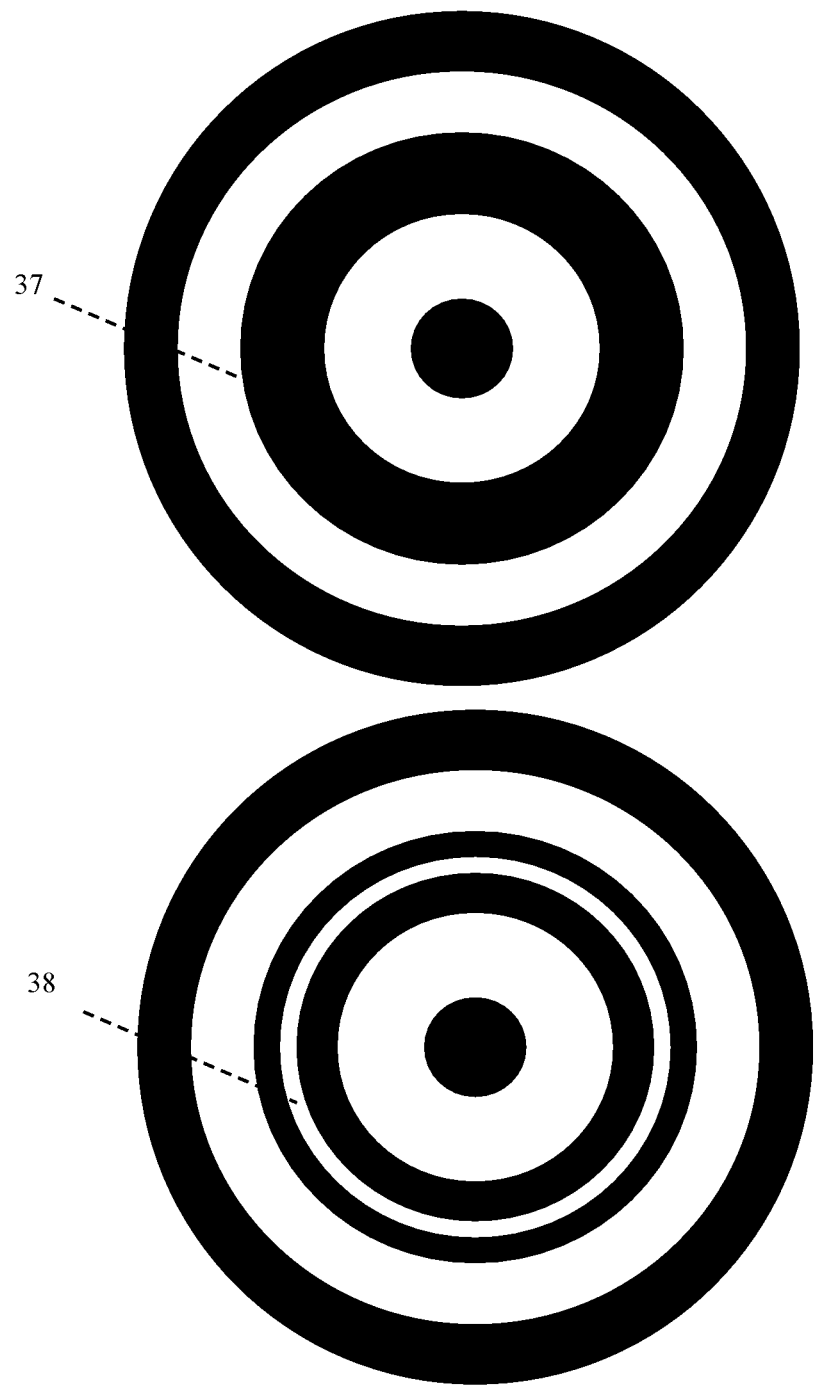
FIG. 7 illustrates a ring pattern for a properly positioned corneal vertex distance and also for an improperly positioned corneal vertex distance according to embodiments.

FIG. 7 illustrates a ring pattern for a properly positioned corneal vertex distance according to embodiments. In embodiments, for example, a central black circle, next white ring and inner half of the next black ring come from a central rings light guide 23 and the second half of the black ring 37 and the rest of the rings come from a peripheral rings light guide 18. In embodiment, as illustrated in FIG. 7, a ring pattern is illustrated for a corneal vertex that is too close to a mobile communication and/or computing device (e.g., the smartphone). In embodiments, a central black circle, a next white ring, a next thin black ring, and a thin white ring 38 may be generated or projected from a central rings light guide 23 and a second thick black ring and a rest of the concentric rings may be generated and/or projected from peripheral rings light guide 18. In embodiments, a corneal topography system and/or an operator may adjust a positioning of a cornea vertex by adjusting a position of the mobile communication and/or computing device 2 (e.g., the smartphone) relative to a subject's cornea until a thin white ring is no longer visible.

In embodiments, if a camera on a mobile communication and/or computing device 2 (e.g., a smartphone) captures a rings image (or images) (e.g., a concentric rings image), if a thin white ring is present, a thin white ring may also be captured in a rings image. In embodiments, if a thin white ring is present in a captured image, this may provide a useful indication that a subject's cornea was not well positioned along an optical axis of a corneal topography system during image acquisition. Likewise, if the two half black rings (one from the central rings light guide and the other from the peripheral rings light guide) overlap so that the appearance is of a thinner than normal black ring, then this can be an indication that the eye was too far away during acquisition. In alternative embodiments, additional apparatus and methods may be utilized to establish proper distance for a subject's eye (and thus cornea) (e.g., a proper vertex distance). In embodiments, for example, proper vertex distance may be ascertained by one or more of the following techniques, methods, apparatus, and/or devices: utilizing angled beams of light directed such that the beams of light intersect in front of the placido disc system only at a corneal apex; projection of two different reticle patterns from each side of a Placido disc system, such that a vertex distance can be identified only by a unique pattern made when may exactly overlap at a specific distance (reticles may be, for example, in the shape of a circle and a "+" sign, with the end-point being visually identified by the + being exactly inside the circle); incorporation of a focusing screen; utilizing an ultrasound range-finding subsystem to be employed to identify a target at a specific distance from an ultrasound transducer; utilizing a single laser beam in conjunction with front view camera to triangulate location; utilizing a single slit projected from the inferior side and utilizing a front view camera to triangulate (which also gets corneal thickness, ACD, posterior cornea curvature (along one meridian)); utilizing a Side view of eye to see vertex (e.g., place on a camera display as a split view acquisition (for example, left side rings, right side cornea side view); and/or utilizing a single OCT ascan to measure distance using short coherence length correlation Returning to top level aspects of a corneal topography apparatus and/or system, FIG. 8 illustrates the auxiliary image lens 20 in relation to an object plane 39 according to embodiments. In embodiments, as is illustrated in FIG. 8, an auxiliary imaging lens 20 is shown relation to an object plane 39 of corneal reflected rings and a mobile communication and/or computing device (e.g., the smartphone) camera aperture 21. In embodiments, an object plane may be approximately 4 mm behind a front surface of a cornea. In embodiments, a focal length of an auxiliary imaging lens may be equal to the distance from a corneal reflected rings object plane 39 to an auxiliary imaging lens 20 so that a camera of a mobile communication and/or computing device (e.g., the smartphone) may see an incoming object at, for example, optical infinity. In embodiments, as illustrated in FIG. 8, optical rays 40 from an object plane to a camera in a mobile communication and/or computing device (e.g., the smartphone) aperture 21 is illustrated.

Figure 9:
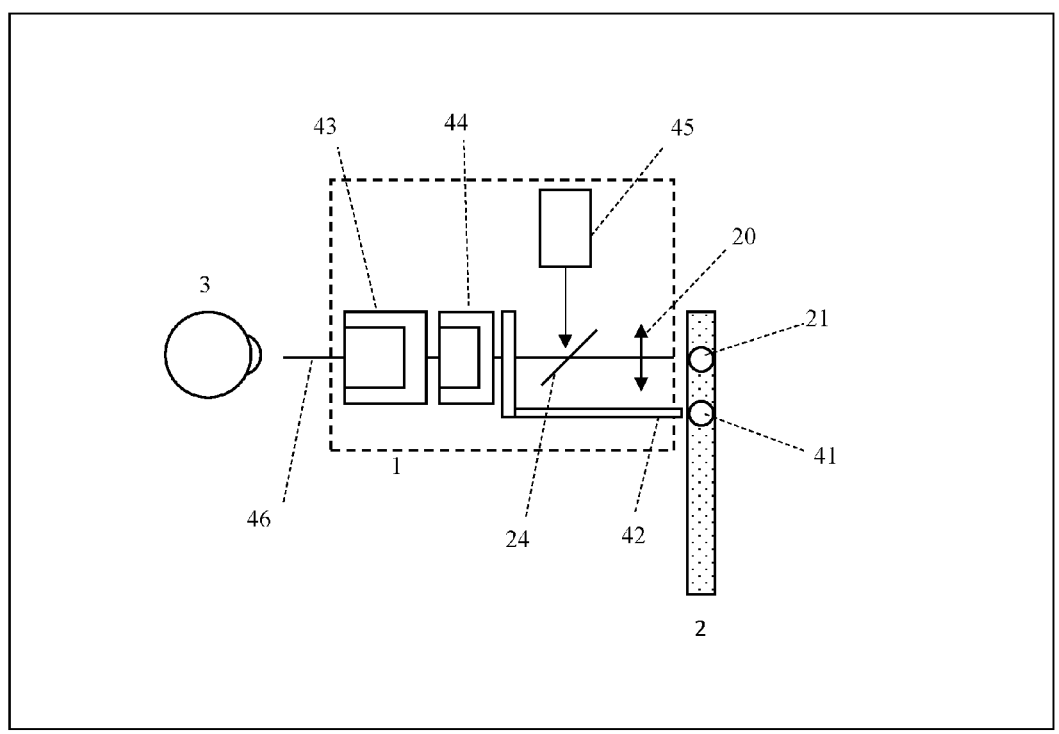
FIG. 9 illustrates an alternative embodiment of a corneal topography system according to embodiments.

In the following, an alternative embodiment is described. FIG. 9 illustrates an alternative embodiment of a corneal topography system according to embodiments. In embodiments, as illustrated in FIG. 9, a corneal topography system or apparatus may comprise, in addition to the portable computing and/or communications device 2 (e.g., smartphone), additional external hardware, assemblies and/or components. In embodiments, FIG. 9 illustrates these additional hardware, assemblies and/or components. In embodiments, a corneal topography system or apparatus may utilize an eye to be measured 3 and may comprise a mobile communication and/or computing device (e.g., a smartphone) 2, a mobile communication and/or computing device (e.g., smartphone) camera aperture 21, a mobile communication and/or computing device (e.g., smartphone) camera light source 41, an auxiliary imaging lens 20, a light coupling light pipe 42, a beam splitter 24, a target light guide 43, a positioning light guide 44, and a fixation light source 45.

In this embodiment, rings which are reflected off the cornea may be generated by target light guide 43. In embodiments, this component may be constructed as a truncated cone with the rings placed on the inside of the cone. The rings may also be constructed as a cylinder (as illustrated in FIG. 9) with the rings placed on an inside (e.g., inside surface) of a cylinder. In addition to cone or cylinder shapes, a plane at the end of the cone or cylinder may be added to simplify addition of central rings. In addition, in embodiments, other shapes such as portions of ellipsoids, spheres, polynomial, or free form surfaces can be used as the target light guide with rings placed on the interior of these shapes.

In embodiments, a light coupling light pipe 42 may transmit and/or direct light and/or light rays from a mobile communication and/or computing device's (e.g., smartphone's) light source 41 to a positioning light guide 44. In embodiments, a positioning light guide 44 may provide and/or direct a source pattern used to determine proper distance of a subject's eye 3. In embodiments, a positioning light guide 44 also may transmit light to a target light guide 43. In embodiments, a target light guide 43 may generate rings which are reflected off a subject's cornea during an exam. In embodiments, a fixation light source 45 may generate a small spot coaxial with an optical axis 46 that a subject looks at during an exam. In embodiments, an optical axis 46 may be run between a subject's eye and a mobile communication and/or computing device's (e.g., smartphone's) aperture 21.

Figure 10:
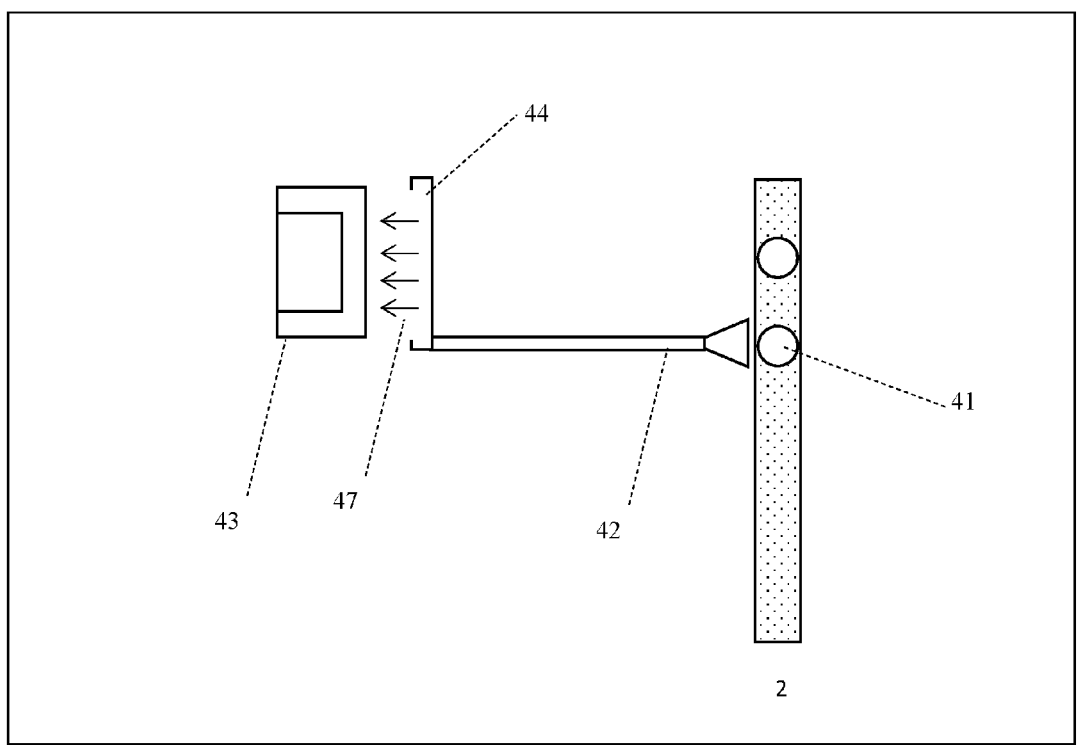
FIG. 10 illustrates additional details of the use of a light source from a mobile communication and/or computing device (e.g., the smartphone)

FIG. 10 illustrates additional details of the use of a light source 41 from a mobile communication and/or computing device 2 (e.g., the smartphone). In embodiments, a light coupling light pipe 42 may collect a majority of light projected or shining from a mobile communication and/or computing device (e.g., the smartphone) light source 41 and deliver the light to a positioning light guide 44. In embodiments, transfer of light to a positioning light guide 44 is illustrated by light rays 47 in FIG. 10. In embodiments, for example, light may be prevented from exiting the light coupling light pipe 42 at other locations using reflective white paint or optical properties such as total internal reflection. In embodiments, a light coupling light pipe 42 is provided so that as custom hardware is integrated with other mobile communication and/or computing devices 2 (e.g., the smartphones), where the mobile communication and/or computing device (e.g., the smartphone) light source 41 is at other locations, only one part may need to be adapted (e.g., the light coupling light pipe 42), which saves time and cost in integrating a corneal topography system with other or updated mobile communication and/or computing devices 2 (e.g., the smartphones).

Figure 11:
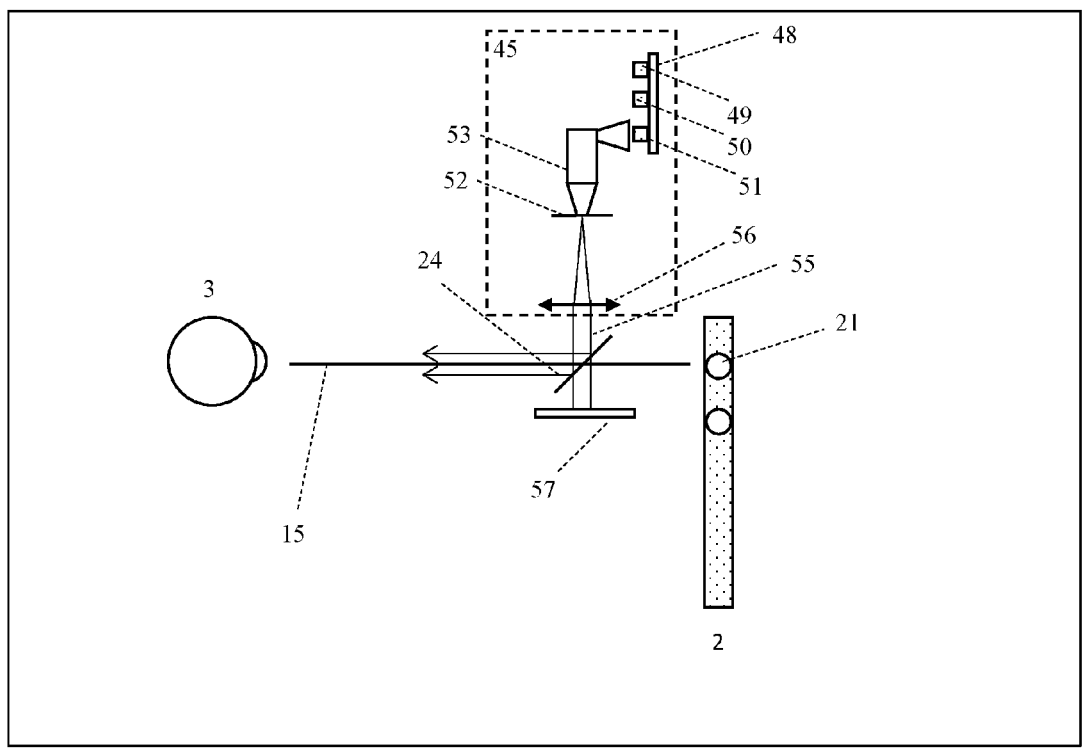
FIG. 11 illustrates a fixation light source according to embodiments.

FIG. 11 illustrates a fixation light source 45 according to embodiments. In embodiments, a printed circuit board 48 may comprise a manual switch 49, a battery 50, and/or a green LED 51. In embodiments, an operator may turn on and/or activate a manual switch 49 prior to an exam and may turn off or deactivate a manual switch after the exam. In embodiments, activation and/or deactivation may occur automatically. In embodiments, a light from a LED 51 may be relayed to an aperture 52 by means of a right angle light pipe 53. In embodiments, a fixation lens 56 may be located a focal length away from the aperture so that light rays 55 exiting a fixation lens 56 are parallel (at optical infinity), as illustrated in FIG. 11. In embodiments, parallel light rays may reflect off a beam splitter 24 which may allow the subject's eye 3 to be properly aligned with an optical axis 15. In embodiments, light rays which may be transmitted through a beam splitter 24 may be absorbed by a beam trap 57 so that rays are not reflected back to a beam splitter 24 and reflected into a mobile communication and/or computing device (e.g., the smartphone) camera aperture 21. In embodiments, instead of a manual switch 49, a mobile communication and/or computing device 2 (e.g., the smartphone) may utilize wireless communications (e.g., a communication channel such as Bluetooth, Zigbee, etc.) and/or Universal Serial Bus (USB) to control activation and/or deactivation of a fixation light source 45. In embodiments, instead of a battery 50, a mobile communication and/or computing device 2 (e.g., the smartphone) may provide power for a fixation light source 45.

Figure 12:
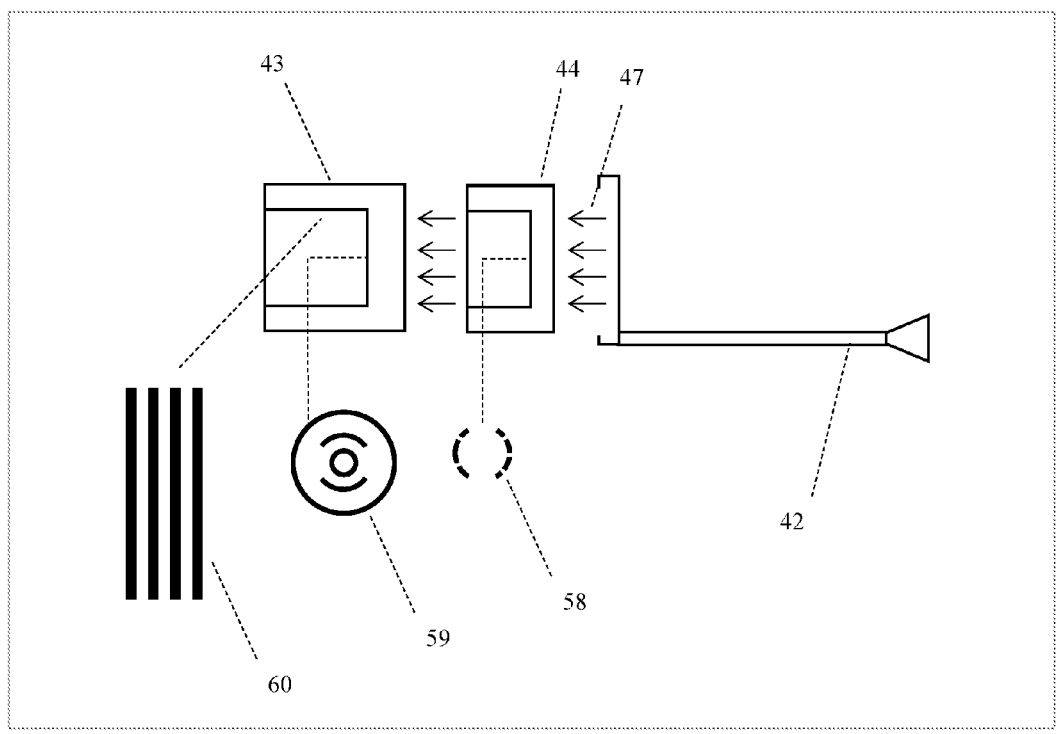
FIG. 12 illustrates a positioning light guide 44 and a target light guide 43 according to embodiments.

FIG. 12 illustrates a positioning light guide 44 and a target light guide 43 according to embodiments. In embodiments, incident light 47 from a light coupling light pipe 42 may be provided to a positioning light guide 44 and may be further propagated to a target light guide 43. In embodiments, a positioning pattern 58 may be placed on an inside surface of a positioning light guide 44. In embodiments, a circle ring target pattern 59 and a parallel ring target pattern 60 may be placed on an inside surfaces of the target light guide 43. In embodiments, these surfaces may be different surfaces. In embodiments, a positioning pattern 58 and/or a circle ring target pattern 59 may work in conjunction with each other to show an operator how to properly locate a subject's eye during an exam and/or also to provide measurements and/or information for a software application to account for an error in the location of a subject's eye. Accounting for an error in location of a subject's eye and/or cornea is described below in regards to calibration and software processing. In embodiments, patterns for a circle ring target pattern 59, a parallel ring target pattern 60, and a positioning pattern 58 may be created as decals, which may be placed on respective light guides. In alternative embodiments, patterns may be created by painting surfaces light guides and/or lathing off paint to reveal a final pattern. In embodiments, exact dimensions for patterns may be calculated using, for example, ray tracing analysis known to those skilled in the art of corneal topography design.

In embodiments, as discussed above, a corneal topography system and/or apparatus includes a software application (e.g., computer-readable instructions stored in a non-volatile memory, that are fetched and/or retrieved, loaded into a volatile and/or non-volatile memory and executed by a processor of a mobile communication and/or computing device (e.g., the smartphone) and/or a computing device and/or server (application server, mobile application server, and/or cloud server)). In embodiments, the corneal topography software may reside on a mobile communication and/or computing device 2 (e.g., the smartphone) and/or on a repository computer 6 (e.g., application server, mobile application server, and/or cloud server). For the purposes of this disclosure, the software may be stored on a computer-readable medium. For purposes of this disclosure, a computer-readable medium stores computer data, which data can include computer program code that is executable by a computer, in processor or computer-readable form. In embodiments, the dividing, location and overlap of individual software functions, computer-readable instructions and/or execution by a processor of the computer-readable instructions is not important and may take place on any device except that control of capturing of and/or acquisition of images of a subject's eye and/or cornea may take place on a mobile communication and/or computing device (e.g., the smartphone) and functionality may be responsive to market forces. In embodiments, In the following description of the methods and/or software execution, there is no indication which functions are relegated and/or assigned to which device and process mobile communication and/or computing device (e.g., the smartphone) or repository computer (e.g., application server, mobile application server, and/or cloud server). Also, fundamental and/or well-known steps of described processes, such as selecting a patient's name from a list, are not detailed in the following descriptions.

Embodiments, such as the processes described below, are intended to be illustrative examples rather than be limiting with respect to claimed subject matter. Likewise, for ease of explanation, an embodiment may be simplified to illustrate aspects and/or features in a manner that is intended to not obscure claimed subject matter through excessive specificity and/or unnecessary details. Embodiments in accordance with claimed subject matter may include all of, less than, or more than blocks 1005-1025, 1105-1140, and 1205-1220. Also, the order of blocks 1005-1025, 1105-1140, and 1205-1220 is merely as an example order.

Figure 13:
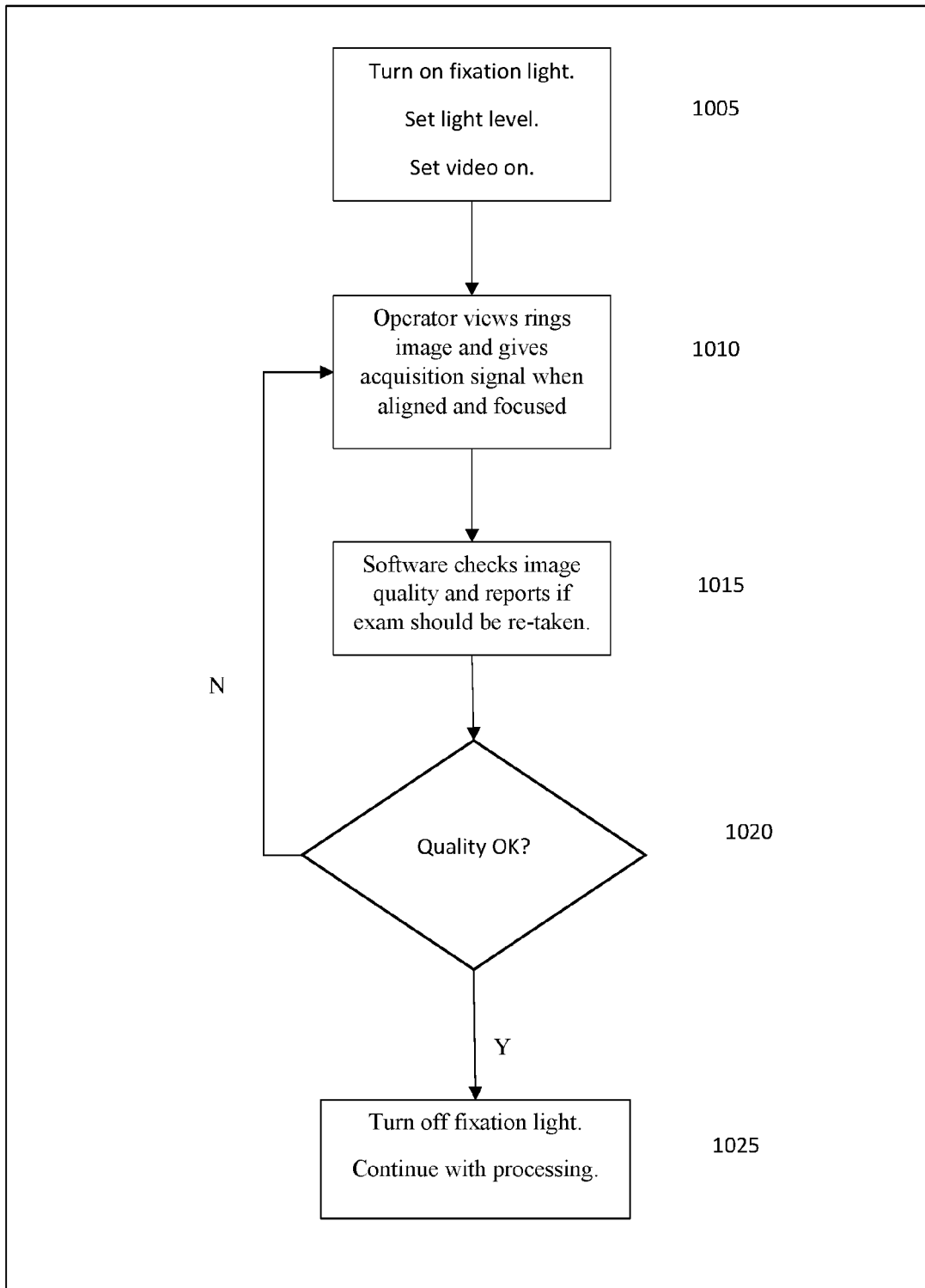
FIG. 13 illustrates an exam image acquisition process according to embodiments.

FIG. 13 illustrates an exam image acquisition process according to embodiments. In embodiments, in basic exam acquisition, the operator may turn on a fixation light, set a light level for rings (selects "Light Iris" or "Dark Iris"), and turn on image capture (e.g., video) 1005. In embodiments, an operator views a live rings image and provides an acquisition signal 1010 (e.g., selects a button) when the image has the following characteristics:

a. Eye is present
 b. Rings are centered
 c. Image is focused
 d. Positioning ring appears continuous In embodiments, software analyzes and/or checks image quality 1015 (e.g., the software analyzes the result of evaluating the above 4 factors). In embodiments, if an image quality is not deemed acceptable, a message is communicated and/or displayed (e.g., to an operator) and a method returns 1020 to live acquisition of images to try and obtain acceptable image quality. In embodiments, if an image quality is acceptable, an operator may manually turn off or deactivate 1025 a fixation light (e.g., fixation light source). In embodiments, processing continues on a captured image.

In embodiments, a second interactive exam acquisition method may occur automatically. In embodiments, image quality may be evaluated automatically on a video frame by frame basis by software running on a mobile communication and/or computing device. In embodiments, when image quality meets and/or exceeds an established threshold, an image of a subject's cornea may be automatically acquired and processing may proceed with a captured image. In embodiments, decisions to utilize a manual and/or automatic exam image acquisition method may be dependent upon a processing power of a mobile communication and/or computing device (e.g., a smartphone), a difficulty of acquiring an exam, operator experience, and/or market forces.

In embodiments, an orientation of a mobile communication and/or computing device (e.g., a smartphone) may recorded at the time of image acquisition. In embodiments, this orientation may be provided by a gyroscope and/or similar device on a mobile communication and/or computing device. In embodiments, a gyroscope generates rotational information and/or vertical information. The software receive the rotational information and/or vertical information and assesses the attachment's/smartphone position with respect to a true vertical position. In embodiments, orientation measurements and/or data may be used to rotate corneal measurement and/or data to maintain, for example, an accurate axis of astigmatism.

Figure 14:
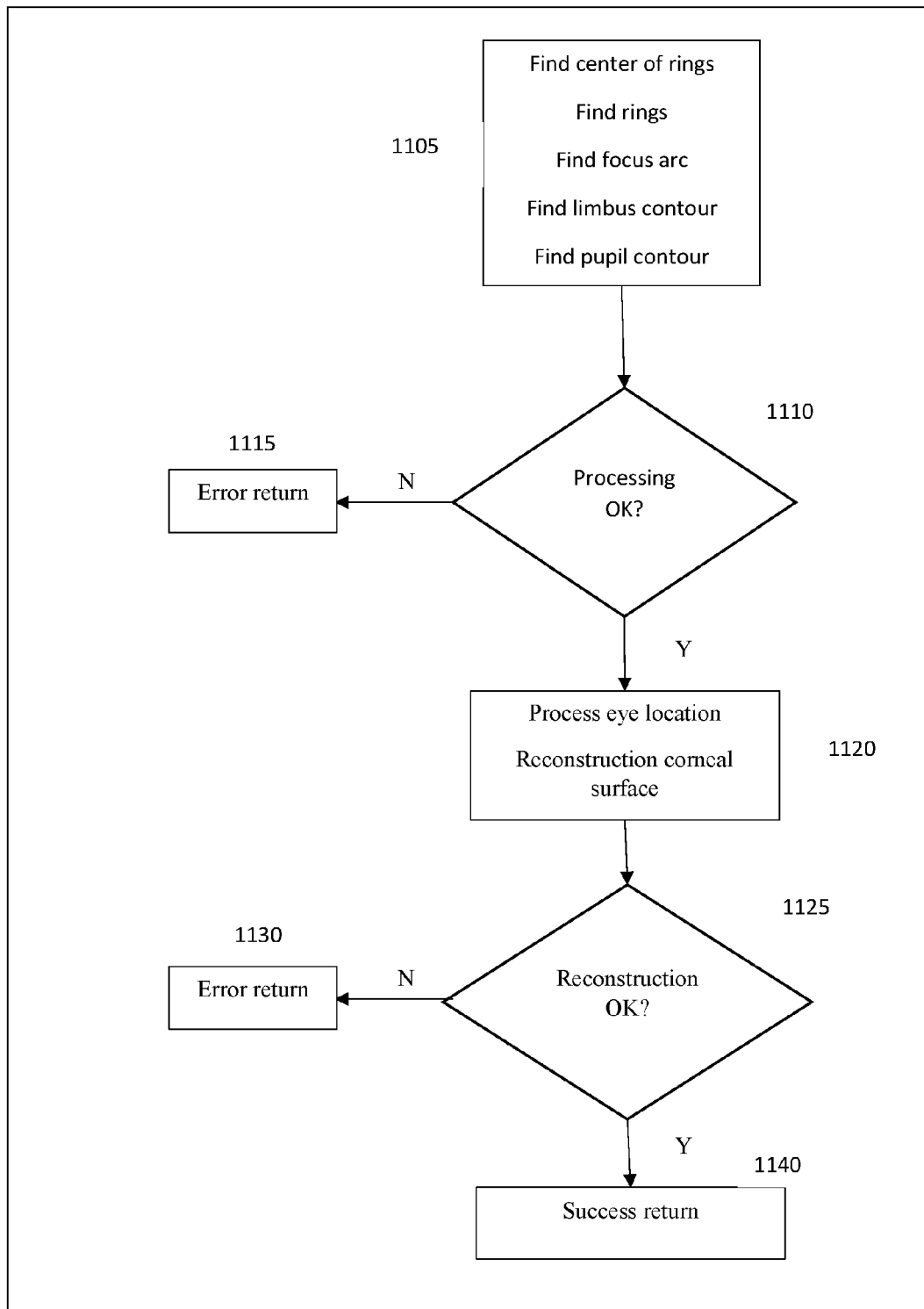
FIG. 14 illustrates an image processing process according to embodiments.

FIG. 14 illustrates an image processing process according to embodiments. In step 1105, a mobile communication and/or computing device (e.g., a smartphone) may perform image process operations on a captured image to: find the center of rings, find all ring edges, find focus arcs, find limbus contour, and/or find a pupil contour. In embodiments, in step 1110 image processing of a captured images is considered a success if all features described above are found or if all features are found except for a pupil contour, otherwise, the image processing is considered a failure. In embodiments, if image processing fails, an error message may be communicated and/or displayed 1115 on a computing device (e.g., a smartphone or a desktop or laptop or tablet computer) for viewing by an operator. The operator is then allowed to attempt to acquire another exam if not successful. In embodiments, if image processing is successful on a captured image, a reconstruction of a cornea may be generated and/or performed 1120 (e.g., by an external computing device such as a repository computer). In embodiments, a repository computer may receive a captured imaged and associated measurements, generate a corneal topography map, and communicate the corneal topography map back to the mobile communication and/or computing device. In embodiments, a reconstruction model of a cornea fails 1125, an error message may be communicated to and/or displayed 1130 on a smartphone or a desktop or laptop or tablet computer. In embodiments, an operator may be allowed to attempt to acquire another exam. If virtual reconstruction of a cornea is successful 1140, corneal data and/or reconstruction data may be saved and results may be communicated to a smartphone or desktop or laptop or tablet and/or presented to the operator. In embodiments, additional analysis on an acquired exam (e.g., captured image) may comprise an exam quality metric and various surface values. This may be performed on a repository computing device or server and/or on a mobile communication and/or computing device.

Figure 15:
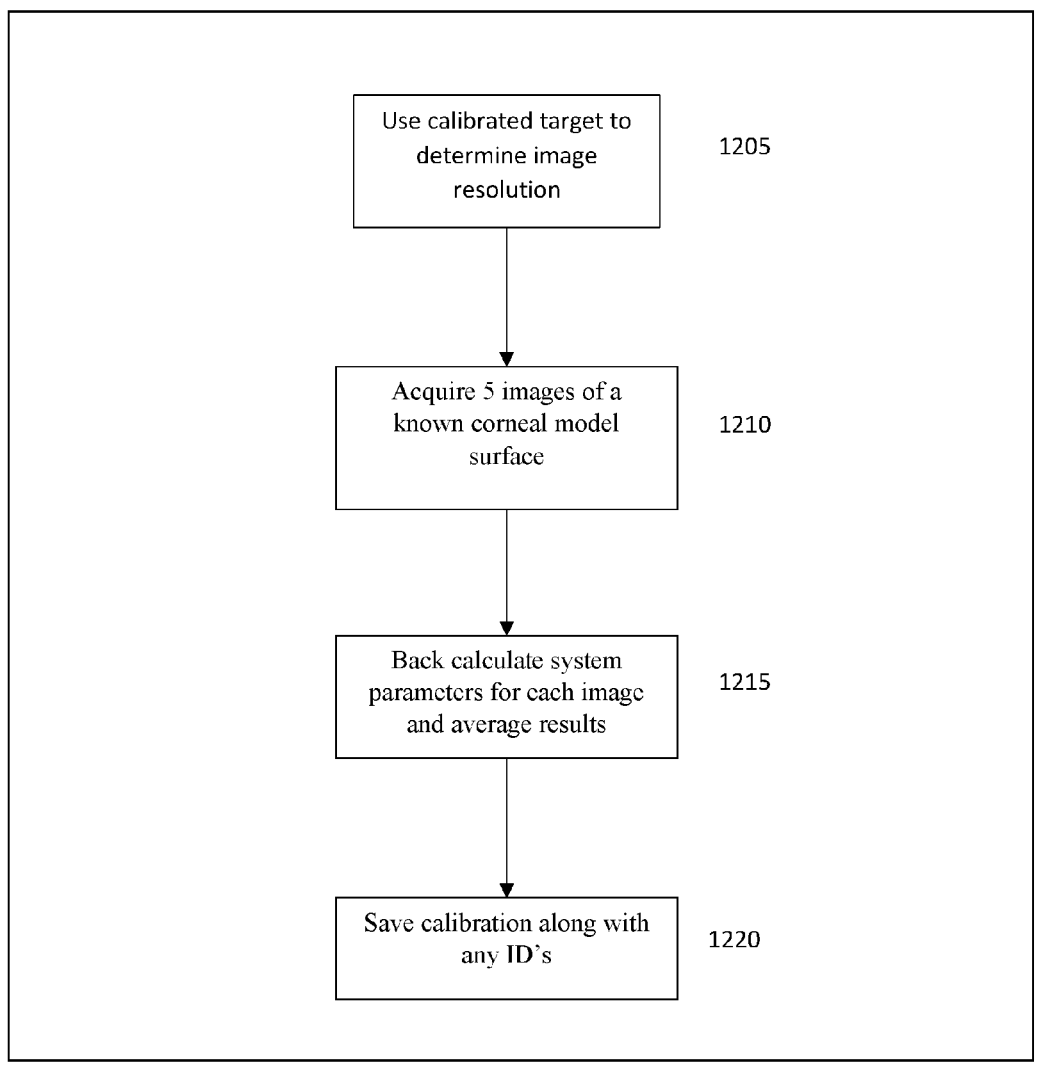
FIG. 15 illustrates a primary calibration process according to embodiments.

FIG. 15 illustrates a primary calibration process according to embodiments. In embodiments, in step 1205, a focused image of a calibrated target may be acquired. In embodiments, a known size of features on a target may be utilized to calculate a resolution of a target. In embodiments, in step 1210, five images of a known corneal surface model, for example, a 7.8 mm spherical surface, may be acquired and processed. In embodiments, in ray tracing, or other analysis, may be utilized to back calculate 1215 system parameters for each reflected ring. In embodiments, the calculated system parameters may be averaged for each of 5 prior acquisitions. In embodiments, in step, calibration data may then be saved and/or stored 1220 along with identifying information about the serial number of corneal topography hardware.

Figure 16:
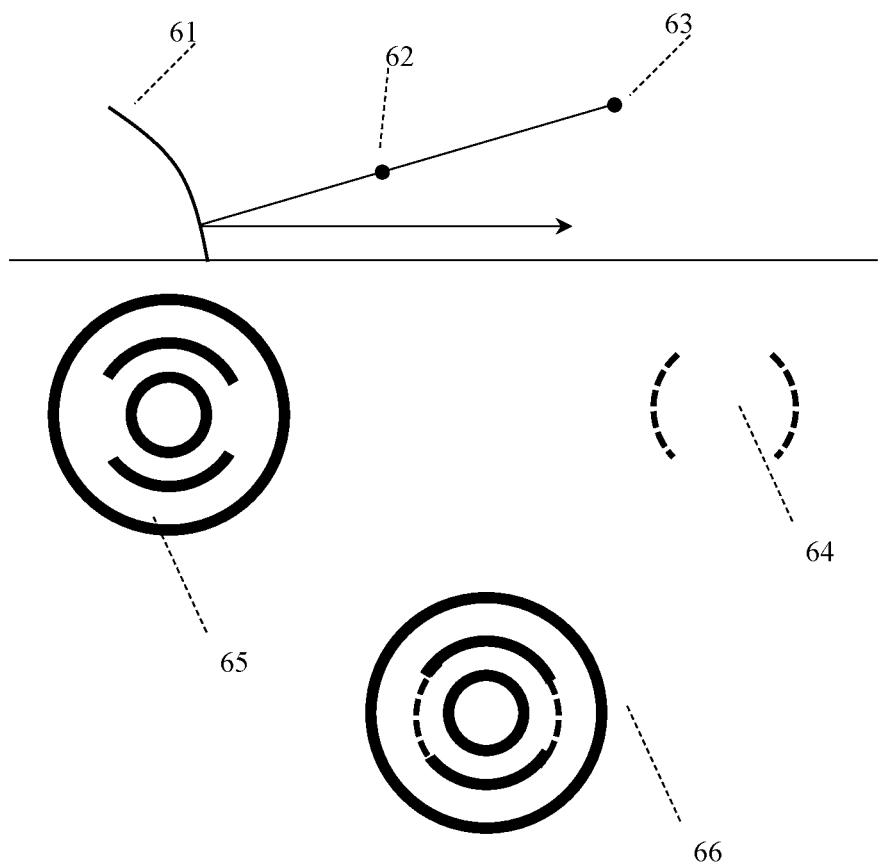
FIG. 16 illustrates a side view of a corneal profile, a point on a ring target, and a point further from the cornea on a positioning light guide according to embodiments.

In addition to an off line calibration of a corneal topography system, a calibration check feature may be performed and/or provided. In embodiments, to check calibration, a known surface (7.8 mm sphere) may be used in place of a subject's eye. In embodiments, an operator may acquire an exam of the surface (e.g., a captured image) and may observe the calculated measurements to determine if a corneal topography system may be within an acceptable tolerance. FIG. 16 illustrates a side view of a desirable case of ring positioning according to embodiments.

In embodiments, FIG. 16 illustrates a side view of a corneal profile 61, a point on a ring target 62, and a point further from the cornea on a positioning light guide 63. In embodiments, below this side view may be patterns for rings reflected from a cornea 65 and a positioning pattern reflected from a positioning light guide 64. In embodiments, a combined image recorded by the camera a reflected pattern 66 is shown below in the FIG. 16. In embodiments, such as for example, illustrated in FIG. 16, a cornea may be at a correct location, and a positioning arc may be aligned with a corresponding target ring, which is a desired case.

Figure 17:
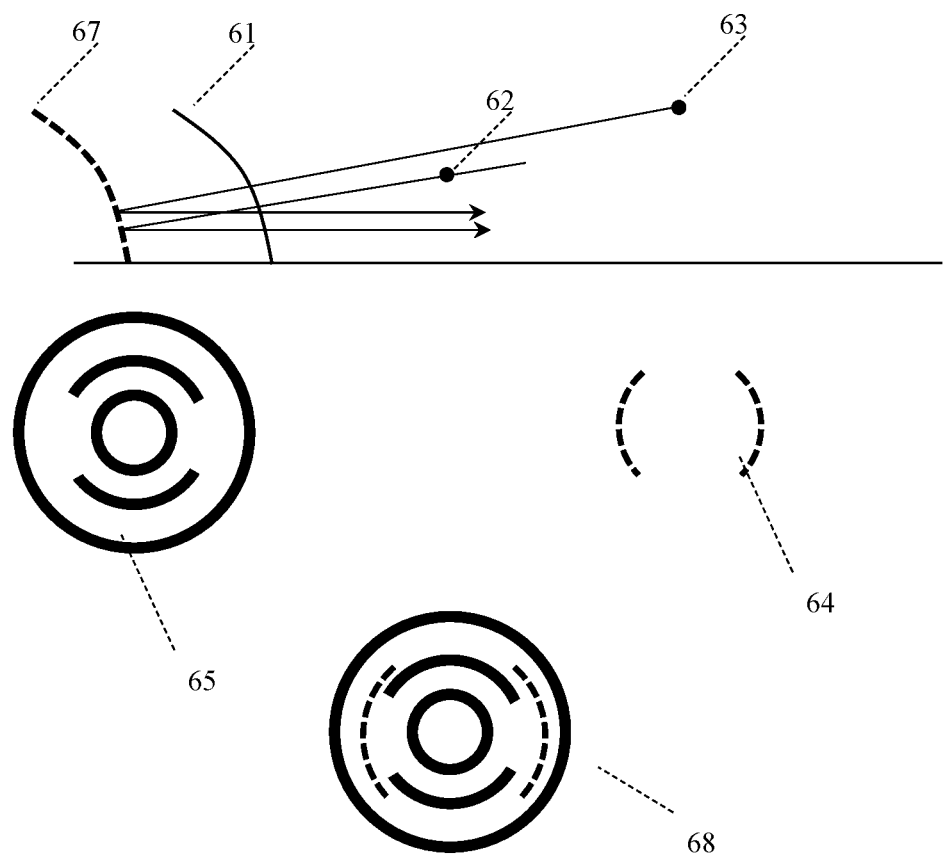
FIG. 17 illustrates a side view when a cornea is too far from ring targets according to embodiments.

FIG. 17 illustrates a side view when a cornea is too far from ring targets according to embodiments. In embodiments, such as illustrated in FIG. 17, a cornea 67 is too far from the ring targets. In embodiments, when this occurs, a positioning arc moves further out and/or away from a corresponding target ring 68.

Figure 18:
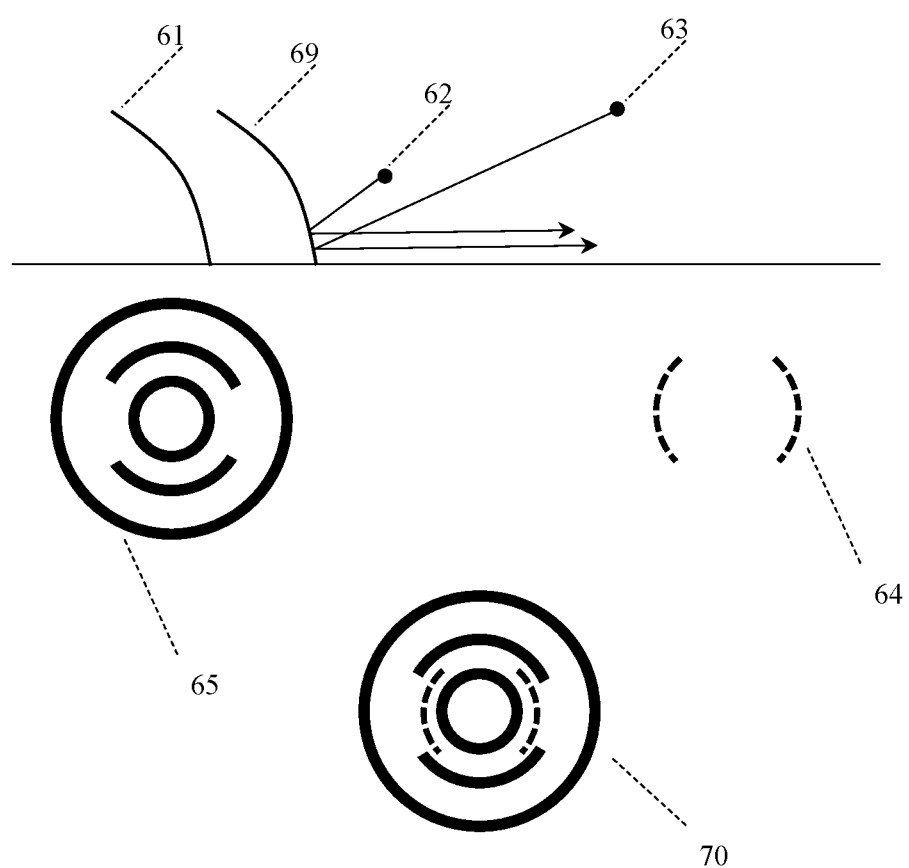
FIG. 18 illustrates a side view when a cornea is too close to ring targets according to embodiments.

FIG. 18 illustrates a side view when a cornea is too close to ring targets according to embodiments. In embodiments, when this occurs, a positioning arc moves closer to a center of the rings than the corresponding target ring 70. Utilizing these techniques and examples from FIGS. 16-18, an operator may visually see when a cornea is at the correct z-position.

Figure 19:
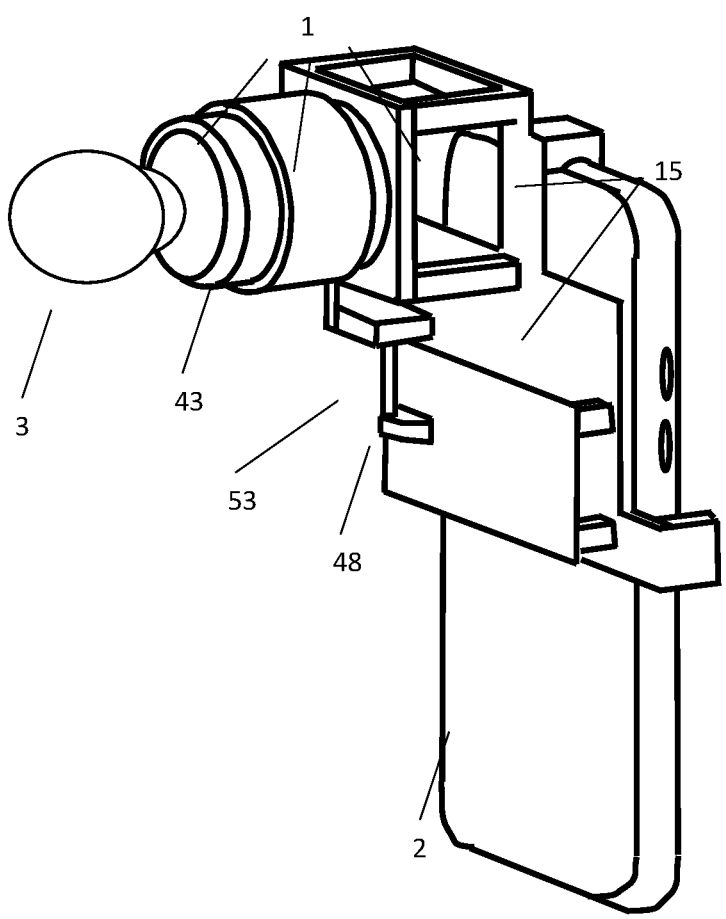
FIG. 19 illustrates a three-dimensional view of the corneal topography system according to embodiments.

FIG. 19 illustrates a three-dimensional representation of a corneal topography system according to alternative embodiments. This figure illustrates only one potential embodiment of a corneal topography apparatus and/or system and is in no way limiting. In embodiments, as is illustrated in FIG. 19, a corneal topography apparatus or attachment 1 may be attached to a mobile communication and/or computing device (e.g., smartphone 2) using a single part frame attachment 15. In embodiments, a subject's eye 3 may look into a target light guide 43 at a fixation spot generated by an LED on a printed circuit board 48. In embodiments, a right angle light pipe 53 may guides the light from an LED on a printed circuit board to a beam splitter (not shown) to align the eye to an instrument.

In embodiments, a system described herein may measure a difference between a positioning arc and a target ring and may correct for a distance during cornea reconstruction. In embodiments, those skilled in the art may calculate an effect of a position shift using ray tracing, or other, analysis. Also, in embodiments, a captured rings image documents or identifies a state of the corneal position during an examination.

In additional embodiment, lights sources, described above, (e.g., peripheral ring lights source 17, a central ring lights source 22, and/or central fixation light source 45, may be individually controlled and/or addressed. In embodiments, this may allow and operator and/or corneal topography system to align a subject's eye at reduced light levels, and/or temporarily increase light levels for acquiring an images to be processed. Utilizing this embodiment, for example, an overall exam may be more comfortable for a subject, who may be dilated or naturally photophobic. In another embodiments, a communication channel, such as a Bluetooth, Zigbee, or other wireless local area network communications channel, may be used between a software application on a mobile communication and/or computing device (e.g., the smartphone) and a corneal topography hardware attachment.

Although a placido ring illumination system in a corneal topography system is described herein, techniques, methods, apparatus, devices and systems described herein may also be utilized for a) measurement of aberrations of an eye using wavefront sensors, such as Hartman screens or Ronchi Grid sensors; b) digital photography of the ocular fundus/retina; c) attachment of a miniature slit-lamp microscope to a smartphone; d) projection topography—uses projected patterns on the cornea and/sclera (typically with fluorescein) to measure a true elevation surface (e.g., primarily used for extended size contact lens designs; and/or e) scanning slit corneal topographer for measuring corneal surfaces, corneal thickness, lens location, and/or surface power.

In embodiments, a mobile communication and/or computing device (e.g., smartphone) may be replaced by a tablet or other low cost or portable computing device; a full feature desktop and/or laptop personal computer and/or an integrated computer on a printed circuit board.

In embodiments, images, measurements, information and/or other data may be communicated in compressed, encrypted and/or encoded form. Further, in embodiments, computing devices (e.g., mobile, portable, servers, etc.) may include components, circuits and/or assemblies to perform compression/decompression; encryption/decryption; and/or encoding/decoding.

In embodiments, a rings target may be back illuminated by either a lighting and/or illumination assembly of a mobile communication and/or computing device (e.g., smartphone) and/or a separate and/or independent custom light source (e.g., light assembly and/or illumination assembly).

In embodiments, a communication channel utilized by a mobile communication and/or computing device (e.g., smartphone) (e.g., Bluetooth, USB, Zigbee, and others), may include a serial number that corresponds to hardware or devices and that may be communicated to the mobile communication and/or computing device (e.g., smartphone) to prevent unauthorized use of a system.

This system and method may be deployed on a "smart" device that communicates with the Internet over Wi-Fi (802.11G and similar) networks rather than cellular (3G) networks. For example, an Apple iPod Touch® contains a hi-resolution camera and processing chipsets comparable to an Apple iPhone®, but does not contain 3G chipsets for cellular communications. This is more than sufficient to host the topography attachment, capture and upload images, download processed power maps, etc.

There are several reasons why the current invention has distinct advantages over prior art. These can be discussed in categories including quantitative accuracy, cost, ease of use, portability, appeal to eye care providers, appeal to providers outside of the eye care profession, and Internet-enabled technology considerations.

Figure 20:
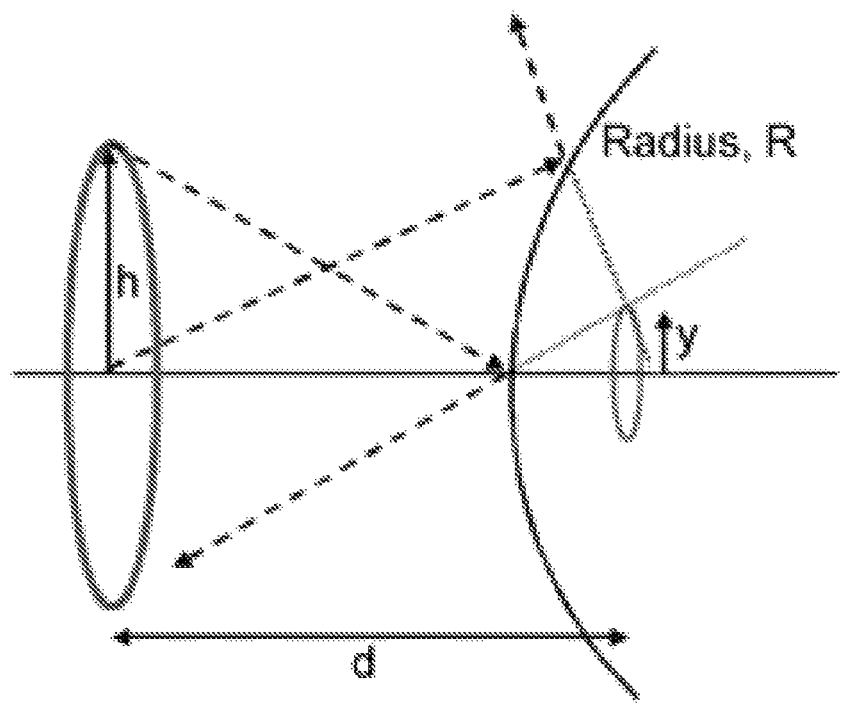
FIG. 20 illustrates vertex distance according to embodiments.

Prior art corneal topography systems are able to detect relative abnormalities of corneal curvature such as keratoconus, but they are not able to measure exact radius of curvature on the corneal surface, as they are unable to establish vertex distance. Vertex distance is the distance from the plane of the placido ring apparatus to the apex of the central cornea being measured, and is identified by the variable "d" in FIG. 20. To measure corneal radius with a keratometer (single ring measurement system), as shown in Equation 1, a ring of known size is placed in front of the eye. The cornea (in reflection) forms a virtual image of the ring below its surface. The virtual image is the first Purkinje image of the ring. The size of this image is related to the radius of curvature, R, of the cornea by R=2dy/h, where h is the radius of the ring object, y is the radius of the ring image, and d is the distance between the object and image. In converting the corneal radius R in millimeters to corneal power P in diopters it is customary to use the keratometric index of refraction nk=1.3375(3) as shown in equation (2).

$$R = 2yd/h \quad (1)$$

$$P = 1000(n\_k - 1.0)/R \quad (2)$$

In contrast, corneal topography systems generally employ surface reconstruction algorithms that calculate surface sag and slope and enforce a surface continuity constraint. Generally, a known distance from the corneal vertex to some point in instrument coordinates is required to start the reconstruction.

Most current corneal topography systems are expensive, costing roughly $8,000 to $55,000 per unit, depending upon features (dual-surface mapping instruments costing more). Even portable systems carry a cost in the $6,000 to $12,000 range, which puts them out of reach of pediatricians, nurse practitioners and the vast majority of eye care providers in the third world. Most eye care providers in the current era only have one corneal topography system in their offices, which means that if all patients are tested on such equipment, it potentially creates a bottleneck to patient flow and clinic throughput. The creation of a smartphone-attached corneal topography system (the smartphone may be substituted by a Wi-Fi-enabled device such as an Apple iPod®) makes it possible to create an entirely unique monetization scheme based on a monthly subscription model rather than any high-cost capital equipment model. We anticipate, for example offering sophisticated corneal topography capability for $50 to perhaps $80 per month, per provider, possibly with discounts for second and third units in a single provider office. This eliminates both the high capital cost of desktop-based platforms tied to motorized examination tables, along with the financial barrier to entry of same. The zero up-front cost and subscription model may open up channels to numerous unit sales previously untapped or under-appreciated.

Currently, there is a broad expansion of Internet-connected devices. Everyone under the age of 80 is now familiar with mobile platforms, graphical user interfaces, and use of "apps" or dedicated software applications on smartphones. Curiously, most ophthalmic diagnostic technology (topographers, autorefractors, aberrometers, etc.) still largely embraces the table-mounted, large-footprint, single-purpose, high capital cost design tied to a desktop computer. Among those systems applicable to smartphone-attached embodiment are corneal topography, autorefraction systems, aberrometry systems, pupillometry systems and the like. If a smartphone-attached corneal topography system is easy to use, it will lend itself to adoption by numerous eye care providers including those desiring a supplemental capability in their main offices, or for use in a satellite office, or for use outside of the office. Additionally, providers outside the eye care arena may find it attractive to use such devices for diagnostic or screening purposes.

It is self-evident that an easily portable smartphone-attached system might have large advantages over fixed-platform systems tied to motorized tables and desktop computers. Simply put, instead of bringing the patient to the diagnostic device, housed in a special room in an eye clinic, it becomes possible to bring the diagnostic device to the patient, wherever in the world that may be.

Eye Care providers may desire to add this technology to existing offices, or to equip satellite offices with same. Rather than bringing patients to a special room containing dedicated-platform diagnostic devices, eye care providers regain the ability to perform corneal topography (and other diagnostic studies) in the traditional "exam lane" consisting of a special chair and stand affixed to slit lamp microscope, phoropter, and visual acuity chart projector. It facilitates the screening of millions of patients of all ages for corneal disease, notably keratoconus, without having them come to an eye care provider's office. Eye care professionals that would not typically have expensive corneal topography systems in their offices, such as retinal specialists, might want to incorporate a low-cost, smartphone-based system into their practices.

The incidence of keratoconus in the general population is quoted in various studies to range between 0.5 and 57 per thousand. Keratoconus typically becomes manifest in the late teens to early 20 but can be identified in patients as young as under 10 years of age. Pediatricians are currently unable to easily and cost-effectively perform any type of screening test for keratoconus, largely due to high cost, large footprint and difficulty of use of existing corneal topography systems. A smartphone-attached corneal topography system costing under $100 per month allows even a pediatrician with a modest-sized practice to screen every patient, leading to earlier diagnosis, more rapid therapy, and better realized visual function for potentially tens or hundreds of thousands of affected patients worldwide.

Current corneal topography systems incorporate a Placido disc with multiple concentric illuminated rings, a camera to capture the image of the rings reflected off of a subject's cornea, and software to perform image processing and mapping. The software typically resides on the disc drive of a dedicated personal computer tied to the topography system. Corneal topography maps can be displayed on the computer monitor or sent to a printer, and raw data can be retained on the topography system or stored on a networked computer such as an Electronic Medical Record ("EMR") system. Data storage is complicated by HIPAA considerations. The vast majority of the Information Technology universe has, however, migrated to a cloud-based storage model. It would be easy and should be self-evident that economies of scale are obtained by storage of patient studies on cloud-based servers. This can be facilitated in a fashion that does not allow HIPAA-sensitive information to be retained on any smartphone used for topography image capture (instead, a unique patient identifier number may be used, for example). Properly implemented, a global system is envisioned that can support the hosting of vast numbers of topography studies, far exceeding the numbers hosted by existing topography platforms. This would enable "big data" analysis and other research opportunities. In a fashion analogous to how voice packets are converted to typed text, Placido ring images of patients can be processed on networked servers to return color-coded corneal topography maps. In addition, sophisticated algorithms may be developed and deployed on network servers for customized analysis of topography studies, if desired by the examining physician or referring physician. Such algorithms may detect keratoconus, or prior LASIK surgery, or other anomalies or changes in corneal curvature consistent with either disease or prior surgery.

For the purposes of this disclosure a computer readable medium stores computer-readable instructions, the computer-readable instructions may include computer program code that is executable by one or more processors. In embodiments, for example, and not being read as limiting, a computer readable medium may comprise computer readable storage media, for tangible or fixed storage of data, or communication media for transient interpretation of code-containing signals. Computer readable storage media, as used herein, may refer to physical and/or tangible storage (as opposed to signals) and may include, without limitation, volatile and non-volatile, removable and non-removable media, implemented and embodied, in any method or technology for the tangible storage of information, such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer and/or processor.

For the purposes of this disclosure, a system or module may be software, hardware, or firmware (or combinations thereof), process or functionality, or component thereof, that performs or facilitates the processes, features, and/or functions described herein (with or without human interaction or augmentation). In embodiments, a module can include sub-modules, subroutines, components, subcomponents. In embodiments, software components and/or subcomponents of a module may be stored on a computer readable medium. In embodiments, systems and/or modules may be integral to and/or installed one or more computing devices (e.g., application servers, mobile application servers, and/or cloud-based servers) may be loaded and executed by one or more processors on one or more computing device. In embodiments, one or more software systems and/or modules may be grouped into an engine and/or an application.

Those skilled in the art may recognize that the methods, apparatus and systems of the present disclosure may be implemented in many manners and, as such are not to be limited by the foregoing exemplary embodiments and/or examples. In other words, functional elements being performed by single or multiple components, in various combinations of hardware and software or firmware, and individual functions, may be distributed among software applications at either the client or server, or multiple computing devices, or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components and/or assemblies, in manners now known or to become known. Thus, myriad software/hardware/firmware combinations may be possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

In embodiments, communications between a mobile computing device or computing device and/or a network device and a wireless network may be in accordance with known and/or to be developed communication network protocols including, for example, global system for mobile communications (GSM), enhanced data rate for GSM evolution (EDGE), 802.11b/g/n, and/or worldwide interoperability for microwave access (WiMAX). In embodiments, a mobile computing device or a computing device and/or a networking device may also have a subscriber identity module (SIM) card, which, for example, may comprise a detachable smart card that is able to store subscription content of a user, and/or is also able to store a contact list of the user. In embodiments, a user may own a mobile computing device or a computing device and/or networking device or may otherwise be a user, such as a primary user, for example. In embodiments, a mobile computing device or computing device may be assigned an address by a wireless network operator, a wired network operator, and/or an Internet Service Provider (ISP). For example, an address may comprise a domestic or international telephone number, an Internet Protocol (IP) address, and/or one or more other identifiers. In other embodiments, a communication network may be embodied as a wired network, wireless network, or any combinations thereof. In embodiments, communications between a mobile computing device or computing device and/or a network device and a wireless network may be in accordance with known and/or to be developed communication network protocols including, for example, global system for mobile communications (GSM), enhanced data rate for GSM evolution (EDGE), 802.11b/g/n, and/or worldwide interoperability for microwave access (WiMAX). In embodiments, a mobile computing device or a computing device and/or a networking device may also have a subscriber identity module (SIM) card, which, for example, may comprise a detachable smart card that is able to store subscription content of a user, and/or is also able to store a contact list of the user. In embodiments, a user may own a mobile computing device or a computing device and/or networking device or may otherwise be a user, such as a primary user, for example. In embodiments, a mobile computing device or computing device may be assigned an address by a wireless network operator, a wired network operator, and/or an Internet Service Provider (ISP). For example, an address may comprise a domestic or international telephone number, an Internet Protocol (IP) address, and/or one or more other identifiers. In other embodiments, a communication network may be embodied as a wired network, wireless network, or any combinations thereof.

Algorithmic descriptions and/or symbolic representations are examples of techniques used by those of ordinary skill in the signal processing and/or related arts to convey the substance of their work to others skilled in the art. An algorithm here, and generally, is considered to be a self-consistent sequence of operations and/or similar signal processing leading to a desired result. In this context, operations and/or processing involve physical manipulation of physical quantities. Typically, although not necessarily, such quantities may take the form of electrical and/or magnetic signals and/or states capable of being stored, transferred, combined, compared, processed or otherwise manipulated as electronic signals and/or states representing various forms of content, such as signal measurements, text, images, video, audio, etc. It has proven convenient at times, principally for reasons of common usage, to refer to such physical signals and/or physical states as bits, values, elements, symbols, characters, terms, numbers, numerals, measurements, content and/or the like. It should be understood, however, that all of these and/or similar terms are to be associated with appropriate physical quantities and are merely convenient labels. Unless specifically stated otherwise, as apparent from the preceding discussion, it is appreciated that throughout this specification discussions utilizing terms such as "processing," "computing," "calculating," "determining", "establishing", "obtaining", "identifying", "selecting", "generating", and/or the like may refer to actions and/or processes of a specific apparatus, such as a special purpose computer and/or a similar special purpose computing and/or network device. In the context of this specification, therefore, a special purpose computer and/or a similar special purpose computing and/or network device is capable of processing, manipulating and/or transforming signals and/or states, typically represented as physical electronic and/or magnetic quantities within memories, registers, and/or other storage devices, transmission devices, and/or display devices of the special purpose computer and/or similar special purpose computing and/or network device. In the context of this particular patent application, as mentioned, the term "specific apparatus" may include a general purpose computing and/or network device, such as a general purpose computer, once it is programmed to perform particular functions pursuant to instructions from program software.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all implementations falling within the scope of the appended claims, and equivalents thereof.

The invention claimed is:

1. An apparatus for enabling corneal topography, comprising:
   an attachment to align a placido disc illumination system with a camera of a mobile communication device, the placido disc illumination system to generate concentric rings, and reflect the concentric rings off a cornea, a portion of the reflected concentric rings being utilized to confirm vertex distance; and
   the mobile communication device to comprise a memory, a processor, the camera and computer-readable instructions,
   the camera to capture an image of the reflected concentric ring;
   the computer-readable instructions being executable by the processor to:
      calculate image quality of the captured image and generate related measurements; and
      communicate the captured image and the related measurements to a cloud-based server via a wireless communication network if the image quality is greater than a defined threshold, the cloud-based server to analyze the captured image and generate a corneal topography map.

2. The apparatus of claim 1, further comprising the computer-readable instructions loaded into the memory and executable by a processor to receive an indication of a correct vertex distance and capture the image of the reflected concentric rings if the indication is received.

3. The apparatus of claim 1, wherein a specific concentric image is displayed when the cornea is at a desired vertex distance and wherein different concentric ring images identify the cornea being closer than or further away from the desired vertex distance.

4. The apparatus of claim 1, the external computing device to analyze the captured image and to generate additional clinical interpretations.

5. The apparatus of claim 1, the external computing device to comprise computer-readable instructions loaded into the memory and executable by the processor to calculate/compute a vertex distance.

6. The apparatus of claim 1, the mobile communication device to receive the generated corneal topography map from the cloud-based server via the wireless communication network.

7. The apparatus of claim 1, the mobile communication device further comprising a gyroscope, the gyroscope generating rotational information and/or vertical information, the computer-readable instructions executable by the processor to receive the rotational information and/or vertical information of the mobile communication device and assess the mobile communication device's position with respect to a true vertical position.

8. The apparatus of claim 1, further comprising a lighting source, the lighting source to illuminate the placido disc illumination system to assist in generating the projected concentric rings image.

9. The apparatus of claim 1, further comprising a mounting assembly, the mounting assembly to mount the attachment and/or mobile communication device on a slit-lamp microscope to enable comfortable positioning of the apparatus in front of a seated subject.

10. An apparatus for enabling corneal topography, comprising:
an attachment to align a placido disc illumination system with a camera of a mobile communication device, the placido disc illumination system to generate concentric rings, and reflect the concentric rings off a cornea, a portion of the reflected concentric rings being utilized to confirm vertex distance; and
the mobile communication device to comprise a memory, a processor, the camera and computer-readable instructions,
the camera to capture an image of the reflected concentric ring:
the computer-readable instructions being executable by the processor to:
calculate image quality of the captured image and generate related measurements of the captured image; and
communicate the captured image and the related measurements of the reflected concentric rings to a cloud-based server via a wireless communication network if the image quality is greater than a defined threshold, the cloud-based server to analyze the captured image and generate a corneal topography map,
the cloud-based server to communicate the corneal topography map and/or additional clinical interpretations to one or more of a remote computing device, a medical records repository computing device, an email server for a registered user and/or consulting specialist, a medical billing computing device, a second computing device comprising computer-readable instructions executable by a processor to perform additional analysis (intra-ocular lens ("IOL") power calculation), or a desktop computing device.

11. A method for performing corneal topography utilizing a mobile communication device, comprising:
illuminating a placido disk illumination system;
projecting, utilizing the placido disk illumination system, a plurality of concentric rings onto a subject's cornea;
capturing, via a camera of the mobile communication device, an image of the plurality of reflected concentric rings;
executing, by a processor, computer-readable instructions stored in a memory of a mobile communication device, the executable computer-readable instructions to:
calculate image quality of the captured image and generate related measurements of the captured image; and
communicate the captured image and the related measurements of the reflected concentric rings to a cloud-based server via a wireless communication network if the image quality is greater than a defined threshold.

12. The method of claim 11, further comprising
generating, by a gyroscope in the mobile communications device, rotational information and vertical information; and
the computer-readable instructions executable by the processor to receive the rotational information and the vertical information of the mobile communications device and assess the mobile communication device's position with respect to a true vertical position.

13. The method of claim 11, further comprising:
receiving a computed cornea topography map from the cloud-based server via the wireless communication network.

* * * * *